United States Patent [19]
Larrick et al.

[11] Patent Number: 6,103,888
[45] Date of Patent: Aug. 15, 2000

[54] MAMMALIAN CATIONIC PROTEINS HAVING LIPOPOLYSACCHARIDE BINDING AND ANTI-COAGULANT ACTIVITY

[75] Inventors: James W. Larrick, Woodside; Susan C. Wright, Saratoga, both of Calif.; Michimasa Hirata, Morioka, Japan

[73] Assignee: Panorama Research, Inc., Mountain View, Calif.

[21] Appl. No.: 09/322,911

[22] Filed: Jun. 1, 1999

Related U.S. Application Data

[62] Continuation of application No. 08/691,280, Aug. 1, 1996, which is a continuation-in-part of application No. 08/313,681, filed as application No. PCT/US93/06731, Jul. 15, 1993, Pat. No. 5,618,675, which is a continuation-in-part of application No. 07/916,761, Jul. 17, 1992, abandoned, which is a continuation-in-part of application No. 07/916,765, Jul. 17, 1992, abandoned.

[51] Int. Cl.$^7$ .................................................. C07H 21/04
[52] U.S. Cl. ............................................ 536/23.5; 514/44
[58] Field of Search .............................. 536/23.5; 514/44; 435/6, 69.1

[56] References Cited

U.S. PATENT DOCUMENTS

| | | |
|---|---|---|
| 4,134,792 | 1/1979 | Boguslaski et al. . |
| 5,618,675 | 4/1997 | Larrick et al. ........................... 435/7.1 |
| 5,627,262 | 5/1997 | Pereira . |
| 5,643,570 | 7/1997 | Theofan et al. . |
| 5,650,392 | 7/1997 | Pereira et al. . |

FOREIGN PATENT DOCUMENTS

WO 9402589  2/1994  WIPO .

OTHER PUBLICATIONS

Hirata, N. et al. "Agglutination of Erythrocytes Sensitized with Re–LPS Elicited by Cationic Protein from Rabbit Granulocytes," Endotoxin: Structural Aspects and Immunobiology of Host Responses; Meeting Abstract, Riva del Sole, Giovinazzo (BARI), Italy (May 29–Jun. 1, 1986).

Tsunoda, N. et al. "Anticoagulant, Antiendotoxin and Anti–Bacterial Activities of Cationic Proteins," *International Conference on Endotoxins Amsterdam II; Abstract, Academic Medical Centre*, Amsterdam, The Netherlands (May 22–23, 1987).

Yoshida, M. et al. "Investigations of Endotoxin Binding Cationic Proteins from Granulocytes as Natural Defense Systems," International Symposium on Endotoxin; Abstract, JICHI Medical School, Japan (May 11–13, 1988).

Shimomura, Y. et al. "Anticoagulant and Antibacterial Activities of Endotoxin–Binding Cationic Protein from Rabbit Granulocytes," XIIth Congr. of the Intl. Society on Thrombosis and Haemostasis; Abstract, Tokyo, Japan (Aug. 19–25, 1989).

Hirata, M. et al. "Interaction of LPS with Cationic Protein From Granaulocytes," IUMS Congress: Bacteriology & Mycology; Abstract, Osaka, Japan (Sep. 16–22, 1990).

Hirata, M. et al. "Modification of LPS Activity by LPS–Binding Progein (cap–18)," The First Congress of the International Endotoxin Society; Abstract, San Diego, CA (May 10–12, 1990).

Hirata, M. et al. "Investigation of Endotoxin Binding Cationic Proteins From Granulocytes; Agglutination of Erythrocytes Sensitized with RE–LPS," *Advances in Experimental Medicine and Biology*, vol. 256, pp. 287–299 (1990).

Larrick, J.W. et al. "Complementary DNA Sequence of Rabbit CAP–18—A Unique Lipopolysaccharide Binding Protein," *Biochemical and Biophysical Research Communications*, vol. 179, No. 1, (Aug. 30, 1991).

Hirata, M. et al., "Bacterial Endotoxins," Fourth Int'l Conference on Endotoxins, Amsterdam, Netherlands, pp. 147–159 (Aug. 1993).

Pungercar, J. et al., *FEBS Letters*, vol. 336, No. 2, pp. 284–188 (Dec. 1993).

Saba et al. *Blood* 31:369–380 (1968).

Saba et al., "Anti–Heparin Activity of Lysomal Cationic Proteins from . . . " *Blood*, vol. 31, No. 3, p. 369 (1968).

Harlow, E. et al. "Antibodies: A Laboratory Manual", pp. 55–136 (1988).

Jawetz, E. et al., *Review of Medical Microbiology*, 11$^{th}$ Edition, p. 208, Chapter 18.

*Primary Examiner*—James C. Housel
*Assistant Examiner*—Ginny Allen Portner
*Attorney, Agent, or Firm*—Townsend and Townsend and Crew

[57] ABSTRACT

Compositions and methods for the treatment and diagnosis of lipopolysaccharide-related conditions and coagulant-related disease are provided. Compositions include polypeptides which are identical or homologous to a certain cationic protein (CAP18) obtained from mammalian granulocytes, particularly including a reactive nitrogen inhibiting peptide (RNIP) fragment found at the carboxy-terminus of CAP18. Polypeptides are capable of binding to LPS and inhibiting LPS-mediated activation of macrophage, as well as interfering with the clotting cascade to inhibit coagulation in conditions such as disseminated intravascular coagulation. Compositions comprising the polypeptides in a suitable pharmaceutical carrier are also provided.

1 Claim, 20 Drawing Sheets

```
HUM  ATGAAGACCC AAAGGGATGG CCACTCCCTG GGGCGGTGTG CACTGGTGCT CCTGCTGCTG TGCCTCTGGC
RAB  ATGGAGACCC ATAAGCACGG ACCTTCCCTG GCCTGCTGCT CACTGCTGCT GCTGCTGCTG TGCCCCCAGC   80

HUM  CATCATTGCC CAGGTCCTCA GCTACAAGGA AGCTGTGCTT CGTGCTATAG ATGGCATCAA CCAGCGGTCC TCGGATGCTA
RAB  CATC---GCC CAGGACCTCA CCTACCGGGA GGCTGTGCTC CGCGCTGTGG ATGCCTTCAA CCAGCAGTCC TCAGAGGCCA   160

HUM  ACCTCTACCG CCTCCTGGAC CTGGACCCCA GGCCCACGAT GGATGGGGAC CCAGACACGC CAAAGCCTGT GAGCTTCACA
RAB  ACCTCTACCG CCTCCTGGAC CCTGAC ATGGACCCTCA AGCAGCTGGA GGATGCGAAG CCATACACCC CGCAGCCTGT GAGCTTTACG   240

HUM  GTGAAGGAGA CAGTGTGCCC CAGGACGACA CAGAGGATTG TGACTTCAAG AAGGACGGGC TGGTGAAGCG
RAB  GTGAAGGAGA CGGAGTGCCC CCGGACACAA TGGAAGCTAC CAGAGCAGTG TGACTTCAAG GAAGATGGGC TGGTGAAGCG   320

HUM  GTGTATGGGG ACAGTGACCC TCAACCAGGC CAGGGGCTCC TTTGACATCA GTTGTGATAA GGATAACAAG AGATTTGCC-
RAB  GTGTGTGGGG ACTGTGACAC GGTACTAGGC CTGGGACTCC TTTGACATCC GCTGCAACAG GGCCAAGAG TCCCCAGAAC   400

HUM  CT-----GCT GGGTGATTTC TTCCGGAAAT CTAAAGAGAA GATTGGCAAA GAGTTTAAAA AAGCTTAAAA GAGAATCAAG
RAB  CTACTGGGCT GCGCAAGCGC TTACGAAAAT TTAGAAACAA GATTAAAGAA AAGCTTAAAA AAATTGGTCA GAAAATCCAG   480

HUM  GATTTTTGC GGAATCTTGT ACCCAGGACA GAGTCCTAGT GTGTGCCCTA CCCTGGCTCA GGCTTCTGGG CTCTGAGAAA
RAB  GGTTGCTGC CGAAACTTGC ACCCAGGACA GTCTGCCCTG GATTACTAGG GTCGGACTC CCCTGGACTC TGAAAAATAA ACTGTGTGAA   560

HUM  TAAACTATGA GAGCAATTTC AAAAAAAAAA
RAB  AGCAACAAAA AAAAAAAAAA AAAAAAAAAA
```

FIG. 9

```
HUM met lys thr gln arg asp gly his ser leu gly arg trp ser leu leu val leu leu leu gly leu val met pro   25
RAB met glu thr his lys his gly pro ser leu ala trp trp ser leu leu leu leu leu gly leu leu met pro HUM leu ala ile ile ala gln val leu ser tyr lys glu ala val leu arg ala ile asp gly ile asn gln arg ser   50
PIG             gln     leu     leu arg tyr arg glu glu ala val leu arg arg ala val asp arg leu asn glu gln ser
RAB pro ala ile     ala gln asp leu thr tyr arg glu glu ala val leu arg arg ala val ala phe asn gln gln ser HUM ser asp ala asn leu tyr arg leu leu asp leu asp pro arg pro thr met asp gly asp pro asp thr pro lys   75
PIG ser glu ala asn leu tyr arg leu leu asp leu glu asp pro gln pro lys ala asp gln asp pro gly tyr pro lys
RAB ser glu ala asn leu tyr arg leu leu asp leu ser met asp pro ala leu asp ala lys asp pro thr pro lys HUM pro val ser phe thr val lys glu thr val cys pro arg thr gln ser pro arg glu asp cys asp phe ile ser  100
PIG pro val ser phe thr val lys glu thr val cys pro pro arg thr gln pro gly leu glu cys asp phe ile ser
RAB pro val ser phe thr val lys glu thr val cys pro arg thr lys trp leu pro glu gln cys asp phe ile ser HUM lys asp gly leu val lys arg cys met gly thr val thr leu asn gln ala arg gly ser phe asp ile ser cys  125
PIG     gln         lys gln cys val gly thr val thr leu asn pro ser ile his glu leu asp ser ile ser cys
RAB glu asp gly leu val lys arg cys val gly thr val thr arg gln tyr ala trp asp ser phe asp ile arg cys HUM lys asp asn lys arg phe ala             leu leu gly asp phe arg lys ser lys glu lys ile gly lys      150
PIG asn glu ile gln gly val
RAB asn arg ala gln gly ser pro glu pro thr gly leu arg lys arg lys arg leu arg asn lys ile lys glu HUM glu phe lys arg ile val gln arg ile lys asp phe leu arg asn leu val pro arg thr glu ser END
RAB lys leu lys lys ile gln gly lys leu pro lys leu ala pro arg thr asp tyr END
```

FIG. 10

MAMMALIAN CATIONIC PROTEINS HAVING LIPOPOLYSACCHARIDE BINDING AND ANTI-COAGULANT ACTIVITY

This application is a continuation of application Ser. No. 08/691,280, filed Aug. 1, 1996, which was a continuation-in-part of application Ser. No. 08/313,681, filed on Sep. 27, 1994, now U.S. Pat. No. 5,618,675, which claimed priority from PCT/US93/06731, filed on Jul. 15, 1993, which was a continuation-in-part of application Ser. No. 07/916,761, filed on Jul. 17, 1992 now abandoned, and of application Ser. No. 07/916,765, filed on Jul. 17, 1992, now abandoned the disclosures of which are incorporated herein by reference.

Portions of this work were supported by NIH Grant No. RO1-GM47720. The United States Government may have certain rights in this invention.

BACKGROUND OF THE INVENTION

1. Field of the Invention

The present invention relates generally to compositions and methods for the treatment and diagnosis of lipopolysaccharide (LPS)-associated diseases, such as Gram-negative sepsis. More particularly, the present invention relates to the preparation and use of certain mammalian cationic proteins for such treatment and diagnosis.

A rational approach for the control of Gram-negative sepsis is to neutralize the toxic effects of lipopolysaccharides which are released during the treatment of the underlying bacterial infection. Cationic antibiotics, such as polymyxin B, bind to and neutralize some types of lipopolysaccharide, but their use is limited by toxicity. Certain LPS-neutralizing monoclonal antibodies recognize common types of LPS, but are not effective against all species of Gram-negative bacteria. Antibodies made to regions of lipopolysaccharide conserved among many species, such as the lipid A core, appear to be ineffective against certain types of LPS. Certain mammalian polypeptides have been identified that bind to LPS. These include LPS-binding protein (LBP) and bactericidal permeability increasing protein (BPI). BPI can neutralize the toxic effects of LPS.

Of particular interest to the present invention, a cationic protein having a molecular weight of approximately 16.6 kD has been identified in rabbit granulocytes. The protein, known as CAP18, has been found to bind to and attenuate the activity of LPS in certain in vitro assays.

For purposes of human therapy and diagnosis, however, it is frequently preferable to utilize a human form of a protein rather than a mammalian homolog. This is particularly true when the human form of the protein differs significantly from other mammalian forms of the homologous proteins. Identification of the human form of a protein, however, can be difficult even when a protein has been isolated and cloned in other mammals, particularly when the amino acid sequence of the human homolog differs significantly from the mammalian prototype(s). It is often desirable to provide human or humanized proteins which are improved in some way over the natural form of the protein. For example, proteins and polypeptides useful for therapy and diagnosis may be truncated or shortened forms of the natural human or other mammalian protein. The therapeutic forms of the proteins and polypeptides may also be modified at certain residues in order to enhance activity of the protein in some desirable manner.

It would be desirable to provide improved methods for the treatment of lipopolysaccharide-associated diseases, such as Gram-negative sepsis. In particular, it would be desirable to identify compositions and methods capable of inhibiting or neutralizing lipopolysaccharide-associated damage which occurs in such diseases. It would further be desirable to provide an isolated and purified mammalian cationic protein capable of binding to lipopolysaccharide and inhibiting or neutralizing its activity. It would be particularly desirable to provide a synthetically or recombinantly produced mammalian cationic protein, such as mammalian CAP18. It would be further desirable to provide isolated and purified human cationic proteins capable of binding to lipopolysaccharide and inhibiting or neutralizing its activity. It would be still further desirable to provide modified forms of human and other mammalian cationic proteins which possess lipopolysaccharide binding activity in combination with other desirable activities, such as anti-coagulation activity.

2. Description of the Background Art

Hirata et al., *AGGLUTINATION OF ERYTHROCYTES SENSITIZED WITH RE-LPS ELICITED BY CATIONIC PROTEIN FROM RABBIT GRANULOCYTES*, in Endotoxin: Structural Aspects and Immunobiology of Host Responses; Meeting Abstract Riva del Sole, Giovinazzo (BARI), Italy, May 29–June 1, 1986, describes the extraction of cationic proteins from rabbit peritoneal granulocytes capable of agglutinating red blood cells sensitized with lipopolysaccharide. Tsunoda et al. (1987), Abstract, International Conference on Endotoxins II, Amsterdam, the Netherlands, May 22–23; page 79, describes activities of a cationic protein from rabbit granulocytes, including anticoagulant activity. Yoshida et al. (1988) Abstract, International Symposium on Endotoxin, Osaka, Japan, May 16–19, page SII-3, describes granulocyte cationic proteins having molecular weights from 2 kD to 70 kD. Shimomura et al. (1989), Abstract 1228, XIIth Congress of the International Society on Thrombosis and Haemostasis, Tokyo, Japan, August 19–25, page 339, describes the anticoagulant and antibacterial activities of rabbit granulocyte cationic proteins. Hirata et al. (1990), Abstract S33-3, IUMS Congress: Bacteriology & Mycology, Osaka, Japan, September 16–22, page 19, describes a cationic protein from rabbit granulocytes having an estimated molecular weight of 18 kD. Hirata et al. (1990), Abstract II-P-87, The First Congress of the International Endotoxin Society, San Diego, Calif., May 10–12, also describes the 18 kD cationic protein from rabbit granulocytes.

Hirata et al. (1990), *Endotoxin*, Friedman et al., eds., Plenum Publishing Co., pages 287–299, describes the partial purification of cationic protein from rabbit granulocytes (rabbit CAP18). The cloning and expression of rabbit CAP18 are described in Larrick et al. (1991) Biochem. Biophys. Res. Comm. 179:170–175. The cloning and expression of mammalian CAP18 are described in co-pending applications Ser. No. 07/916,761 and Ser. No. 07/916,765, the full disclosures of which are incorporated herein by reference. These applications also describe an active carboxy-terminal fragment of CAP18 designated the reactive nitrogen inhibitory protein (RNIP). Saba et al. (1967) J. Clin. Invest. 46:580–589 and (1968) Blood 31:369–380, described the presence of cationic proteins having anti-coagulant activity in granulocytes.

SUMMARY OF THE INVENTION

The present invention provides compositions and methods useful for the treatment and diagnosis of certain lipopolysaccharide-associated conditions, such as Gram-negative sepsis and/or treatment of coagulation-related disorders, such as disseminated intravascular coagulation (DIC). The compositions include certain isolated and purified mammalian cationic proteins and polypeptides having a molecular weight from 2 kD to 80 kD, which cationic proteins are capable of binding to lipopolysaccharide to inhibit lipopolysaccharide activity in vitro and in vivo. At least some of the proteins and polypeptides of the present invention will also possess a high affinity binding site for heparin and will display anti-coagulant activity. The compositions further include isolated polynucleotides and genes which encode the mammalian cationic proteins as well as DNA constructs suitable for expressing the genes in cell culture. In this way, the isolated and purified polypeptides may be recombinantly produced in cell culture. The isolated and purified polypeptides are then used in therapy by administering to a host at risk of or suffering from a lipopolysaccharide-associated condition and/or coagulation-related disorder. Additionally, the polypeptide composition may be used for diagnosing patients suffering from such lipopolysaccharide-associated conditions. Such diagnostic methods will comprise exposing a patient sample, typically blood, to the cationic proteins and detecting binding between said proteins and lipopolysaccharide which may be present in the sample.

BRIEF DESCRIPTION OF THE DRAWINGS

FIG. 9 is a comparison of CAP18 cDNA sequence homology in human and rabbit. SEQ ID NO:1 sets forth the human cDNA sequence, and SEQ ID NO:3 sets forth the rabbit cDNA sequence.

FIG. 10 is a comparison of the amino acid sequence homology of the proteins encoded by the cDNA sequences of FIG. 1 as well as pig cathelin. The human amino acid sequence is set forth in SEQ ID NO:2, the rabbit amino acid sequence is set forth in SEQ ID NO:4, and the pig cathelin sequence is set forth in SEQ ID NO:5.

DESCRIPTION OF SPECIFIC EMBODIMENTS

Figure 1:
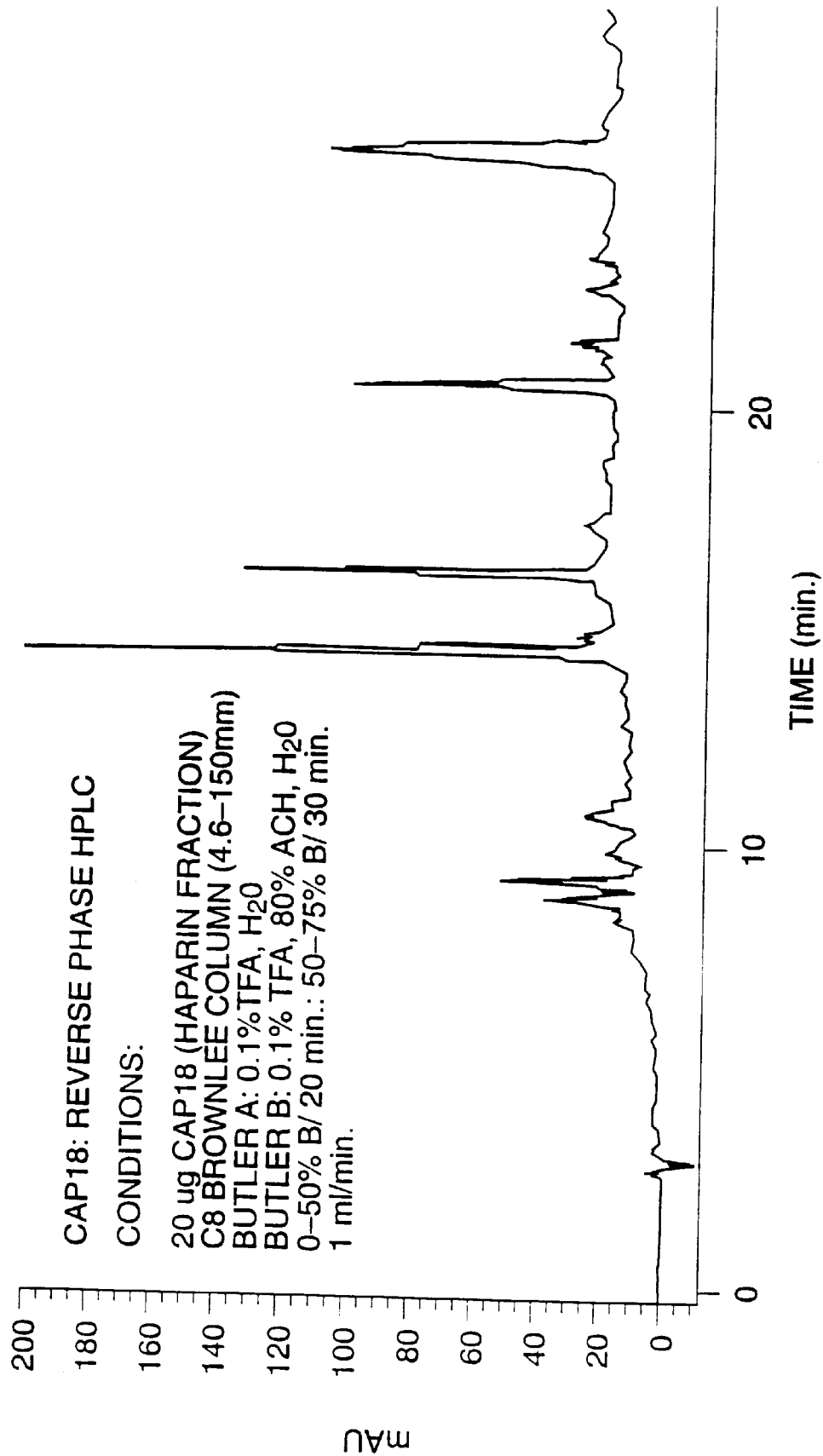
FIG. 1 is a reverse-phase HPLC produced from neutrophil-derived, heparin-bound cationic proteins as described in the Experimental section.

The present invention provides compositions and methods for treating and diagnosing certain lipopolysaccharide (LPS)-associated conditions, such as Gram-negative sepsis and/or coagulation-related disorders, such as disseminated intravascular coagulation (DIC). Gram-negative sepsis occurs as a result of infection of a host with Gram-negative bacteria, where treatment with antibiotics often exacerbates the condition by the massive release of LPS which can accelerate the inflammatory process and cause significant tissue damage. Disseminated intravascular coagulation is a hemorrhagic syndrome which occurs following an uncontrolled activation of patient's clotting factors and/or fibrinolytic enzymes throughout the small blood vessels. As a result, fibrin is deposited and platelets and clotting factors are consumed. Fibrin degradation products inhibit fibrin polymerization, resulting in tissue necrosis and bleeding.

At the present time, certain aspects of the immunoinflammatory cascade initiated by LPS are known in some detail. LPS is known to bind to at least one LPS binding protein (LBP) which is present in plasma and which is known to be induced 10-fold from hepatocytes. LPS bound to this protein binds to CD14, a leukocyte differentiation antigen that transmits a second messenger signal to monocytes to augment synthesis of many important enzymes and mediators, such as interleukin 1 (IL1), tumor necrosis factor (TNF), tissue factor, and nitric oxide synthetase. These molecules contribute to the capillary leak syndrome and tissue injury associated with endotoxinemia.

Certain of the therapeutic and diagnostic aspects of the present invention rely on binding of LPS with a particular natural cationic protein (and derivatives thereof) produced by mammalian leukocytes, particularly granulocytes, such as rabbit granulocytes as described in the Experimental section hereinafter. These cationic proteins will generally have a molecular weight in the range from 2 kilodaltons (kD) to 80 kD, usually from 10 kD to 20 kD, and a pI in the range from 8 to 11, usually from 9 to 10. The cationic protein obtained from rabbit granulocytes has a calculated molecular weight (based on its amino acid sequence) of 16.6 kD and a PI of 10. This rabbit granulocyte cationic peptide has previously been designated CAP18, based on its previously estimated molecular weight. Homologous mammalian cationic proteins from other species, including human, will generally be referred to as CAP18 hereinafter and in the claims.

CAP18 may be identified by conventional protein isolation and purification techniques in combination with in vitro assays which identify its capacity to bind and hemagglutinate LPS-sensitized sheep red blood cells (SRBC). The details of a particular purification procedure are set forth in the Experimental section hereinafter.

CAP18 was first cloned in rabbit, as reported in the Experimental section hereinafter. Surprisingly, the human form which has been cloned and sequenced herein displays an amino acid sequence homology of only about 70% with the rabbit form, with amino acid sequence homology in the RNIP region (described below) being less than 38%. Such low sequence homology rendered cloning of the human analog difficult, as described in more detail hereinafter in the Experimental section.

The human form of CAP18 and CAP18 RNIP have also been found to inhibit bacterial proliferation of Gram-negative bacteria and, to a lesser extent, Gram-positive bacteria. Rabbit RNIP, in contrast, is able to inhibit the growth of both Gram-negative and Gram-positive bacteria, with a generally greater activity than displayed by the human RNIP. Human RNIP has also been found to be free from anti-coagulant activity. Rabbit RNIP, in contrast, has been found to inhibit the coagulation cascade through binding to factor Xa.

CAP18 appears to play a role in the vertebrate inflammatory response and is able to bind most forms of LPS and neutralize LPS-mediated activation of monocytes. CAP18 includes a short peptide, usually present at its carboxy-terminus, referred to as the reactive nitrogen inhibitory peptide (RNIP) which by itself is able to inhibit activation of macrophages. It is presently believed that LPS released by Gram-negative bacteria combines with LPS binding protein (LBP) to provide an activation signal by binding to CD14 on macrophages. Such activation of the macrophages can potentiate a variety of LPS-associated conditions, such as sepsis.

CAP18 and active fragments thereof are able to inhibit or attenuate the activation of macrophages and can thus be useful in the treatment of such LPS-associated conditions. It is presently believed that binding of CAP18 to LPS provides an inhibitory signal to the macrophages via the RNIP fragment. The correctness of this mechanism, however, is not central to the present invention which does not depend on the particular mechanism of activity.

The RNIP fragment of CAP18 from certain species, particularly rabbit, also displays anti-coagulant activity in standard in vitro clotting assays, including prothrombin time (PT) assays, partial thromboplastin time (PTT) assays, and activated partial thromboplastin time (aPTT) assays. The RNIP fragment also has a high binding affinity for heparin. The anti-coagulation activity of the RNIP peptide appears to occur at the activation of prothrombin (factor II to factor IIa). RNIP is shown to inhibit both *Echis carinatus* venom activation of purified factor II to factor IIa as well as factor II activation of by factor Xa formed by incubation of tissue factor, factor VII and factor X, as demonstrated in the Experimental section hereinafter. Thus, the anti-coagulant activity appears to derive from inhibition of at least two sites in the clotting cascade, i.e., the activation of factor X and the activation of prothrombin. While the precise mechanism of inhibition is not clear, as both these coagulation steps require the binding of phospholipids, it is possible that the RNIP peptides interfere with such binding. The fact that factor X activation by Russell Viper venom and prothrombin activation by *Echis carinatus* venom does not require phospholipid binding, however, suggests that the RNIP peptide inhibition of the clotting cascade may be rather complex.

In a first aspect of the present invention, isolated and purified CAP13 polypeptides are provided for use in diagnostic and therapeutic procedures. By "isolated and purified," it is meant that the polypeptides have been isolated from their cellular source and purified to a desired degree of purity, as described in detail hereinafter. Such isolated and purified polypeptides will comprise at least about 9 amino acids, usually being from 25 to 175 amino acids, more usually being from 25 to 150 amino acids. The polypeptides will be identical or homologous to a natural sequence within a mammalian CAP18 molecule, such as the sequence of human CAP18 set forth in SEQ ID NO:2 and the sequence of rabbit CAP18 set forth in SEQ ID NO:4.

Of particular use in the present invention are polypeptides which comprise at least the active portion of the RNIP fragment of the CAP18 molecule and those which comprise substantially the entire CAP18 molecule.

The polypeptides of the present invention will generally have at least about 60% sequence homology with a natural mammalian CAP18 sequence, such as that provided in SEQ ID NO:2 and/or SEQ ID NO:4, usually having at least about 80% sequence homology, more usually having at least about 90% sequence homology, and frequently having 95% sequence homology or greater. Mere sequence homology, however, will not necessarily be sufficient to provide a polypeptide according to the present invention. It will also be necessary that the polypeptide have the ability to bind with most or all forms of LPS and usually be able to inhibit the activation of macrophages, as described above.

In many cases, it will also be desirable that the polypeptide will possess anti-coagulant activity, as measured by conventional assays, e.g., the PT assay, the PTT assay, and the aPTT assay, as described in more detail in the Experimental section hereinafter.

In some cases, it will be preferred that the polypeptides of the present invention be substantially identical to a natural mammalian CAP18 or RNIP polypeptide. By "substantially identical," it is meant that amino acid sequence will either have the identical sequence as that set forth in SEQ ID NO:2 on a residue-by-residue basis, or will have a limited number of amino acid insertions, deletions, or substitutions, where such changes in the amino acid sequence do not significantly alter the activity of the protein. Usually, there will be fewer than 5 insertions, deletions, and/or substitutions in the 37 amino acid RNIP region of SEQ ID NO:2, preferably being fewer than 3 insertions, deletions, and/or substitutions, and more preferably being fewer than 2 insertions, deletions, and/or substitutions. The polypeptides will also retain their "human" nature, i.e. they will be generally recognized as human when administered to human hosts.

In some cases, it may be desirable to replace one or more amino acids in the human RNIP (amino acids 134–170 in SEQ ID NO:2) with non-homologous amino acids in rabbit RNIP (amino acids 135–171 in SEQ ID NO:4). It has been found that the human RNIP is generally less active than the rabbit RNIP, particularly in anti-bacterial activity against gram-positive bacteria. It is believed that substitution of basic amino acids from rabbit RNIP, such as LYS and ARG for non-basic amino acids in human RNIP, such as GLY,. ASP, PHE, and LYS, would enhance the activity of the human peptide without loss of the human nature of the peptide.

In particular, it is believed that the basic amino acids near the amino terminus of rabbit RNIP are responsible for both the greater LPS-binding activity and the existence of the anti-coagulant activity of rabbit RNIP when compared to human RNIP. This belief is based on evidence presented in the Experimental section hereinafter, where various modified rabbit RNIP peptides are tested, with deletions of the basic amino acids at the amino terminus resulting in loss of both LPS-binding activity and anti-coagulant activity. Additionally, it is shown that truncation of at least some of the carboxy terminal amino acids, including at least the five carboxy terminal amino acids of rabbit RNIP, results in only minor loss of activity.

For these reasons, preferred RNIP peptides according to the present invention will be based on the human RNIP sequence (including amino acids 134–170 of SEQ ID NO:2) having at least one of the ARG-LYS-ARG sequence of rabbit RNIP (amino acids 137–139 of SEQ ID NO:4) substituted for at least one of the GLY-ASP-PHE sequence at positions 136–138 of human RNIP, where such substitutions would be expected to enhance LPS-binding activity and/or anti-coagulant activity of the human RNIP. Preferably two, and more preferably all three substitutions will be made. Preferred polypeptides will include at least 25 amino-terminal amino acids of the sequence set forth in SEQ ID NO:6 which represents human RNIP with the preferred ARG-LYS-ARG substitution. Preferably, polypeptides will include at least the 30 amino-terminal amino acids, more preferably including at least 32 amino-terminal amino acids, and may include the entire 37 amino acid sequence.

```
    1                                        10
LEU-LEU-ARG-LYS-ARG-PHE-ARG-LYS-SER-LYS      SEQ ID NO:6

11                                        20
GLU-LYS-ILE-GLY-LYS-GLU-PHE-LYS-ARG-ILE 21                                        30
VAL-GLN-ARG-ILE-LYS-ASP-PHE-LEU-ARG-ASN 31               37
LEU-VAL-PRO-ARG-THR-GLU-SER
```

In a second aspect, the present invention provides isolated polynucleotides corresponding to all or part of a mammalian CAP18 gene in a variety of useful forms. Such polynucleotides include both DNA and RNA sequences corresponding to at least a portion of the CAP18 gene (coding or noncoding sequences), usually including a sequence of at least about 10 contiguous bases within the gene and frequently including up to the entire length of the gene. As a particular example, the polynucleotide sequence may encode (or be complementary to a strand which encodes) the amino acids of the RNIP fragment of a CAP18 molecule, or of the entire CAP18 molecule, or any fragment of the CAP18 molecule which retains a useful activity of the intact molecule.

The polynucleotides of the present invention may also include bases which do not correspond to the structural region of the CAP18 gene, for example, including control regions, linkers, or the like, when the polynucleotide is going to be used to produce recombinant gene product, and other regions which may facilitate the manipulation and/or expression of the polynucleotide. The polynucleotide may also include the structural region(s) of other unrelated genes, particularly when it is desired to produce a fused gene product.

Correspondence between the polynucleotide and the CAP18 gene generally means that the polynucleotide will have a high degree of sequence homology with the naturally-occurring mammalian gene, usually having at least about 40% homology, more usually having at least about 65% sequence homology, and preferably having at least about 90% sequence homology. It will be appreciated, however, that such a high degree of sequence homology will not always be necessary, particularly when the polynucleotide is being used as a portion of a recombinant DNA construct to produce polypeptides corresponding to the natural CAP18 gene product. Because of the redundant nature of the genetic code, substantial nucleotide substitutions can be made without significantly changing the amino acid constitution of the polypeptide being produced. It is only essential that the polynucleotide encode the desired polypeptide, i.e. one having an amino acid sequence having a particular homology with the product of the naturally occurring gene, as discussed above. In many cases, it may even be preferable to provide substitutions within the polynucleotide, e.g., when the recombinant DNA construct is to be expressed in a prokaryotic system, it will frequently be desirable to utilize codons preferentially recognized by the expression host. Additionally, correspondence intends that the single-stranded polynucleotides will be capable of hybridizing with either the DNA strand of the naturally occurring gene, or to the mRNA transcripts produced by the gene, under varying degrees of stringency. cDNA sequences for rabbit CAP18 and human CAP18 have been obtained as described in detail in the Experimental section hereinafter. The sequences are set forth in SEQ ID NO:1 (human CAP18) and SEQ ID NO:3 (rabbit CAP18).

Homologous CAP18 genes from other species may be identified and cloned using probes based on the rabbit and/or CAP18 genes. Probes may be derived directly from the rabbit or human CAP18 cDNA, or degenerate probes may be prepared synthetically based on the nucleotide sequence and/or amino acid sequence provided in SEQ ID NOS:1, 2, 3, and 4. The probes may then be used to screen suitable gene libraries, particularly libraries derived from mammalian bone marrow cells.

Alternatively, other mammalian CAP18 genes may be obtained by first isolating the homologous polypeptide from a suitable cellular source, at least partially sequencing the polypeptide, and preparing degenerate probes based on the deduced amino acid sequence. Such a screening technique is analogous to that used for identifying rabbit granulocyte CAP18, as described in the Experimental section hereinafter.

Suitable other mammalian gene libraries can be obtained from bone marrow cells, as described above. The CAP18 polypeptides may be utilized for synthesizing the CAP18 polypeptides of the present invention by expression in cultured cells of recombinant DNA molecules encoding a desired portion of the mammalian CAP18 gene. The mammalian CAP18 gene may itself be natural or synthetic, with the natural gene obtainable from cDNA or genomic libraries using degenerate probes as described above. Specific rabbit cDNA and human cDNA clones are described in detail in the Experimental section hereinafter. Alternatively, polynucleotides may be synthesized by well-known techniques. For example, single-stranded DNA fragments may be prepared by the phosphoramadite method first described by Beaucagen Carruthers (1981) Tett. Letters 22:1859–1862. A double-stranded fragment may then be obtained, either by synthesizing the complementary strand and annealing the strands together under appropriate conditions, or by adding the complementary strand using DNA polymerase with an appropriate primer sequence. The preparation of synthetic DNA sequences is conveniently accomplished using automated equipment available from the suppliers, such as Applied Biosystems, Inc., Foster City, Calif.

The natural or synthetic DNA fragments coding for the desired CAP18 fragment will then be incorporated into a DNA construct capable of introduction to an expression in in vitro cell culture. Usually, the DNA constructs will be suitable for replication in a unicellular host, such as yeast or bacteria. Alternatively, it may be desirable to introduce and integrate the DNA constructs into the genome of the cultured mammalian or other eukaryotic cell lines. DNA constructs prepared for introduction into bacteria or yeast will include a replication system recognized by the host, the CAP18 DNA fragment encoding the desired polypeptide product, transcriptional and translational initiation regulatory sequences joined to the 5 prime-end of the CAP18 DNA sequence, and transcriptional and translational termination regulatory sequences joined to the 3 prime-end of the CAP18 sequence. The transcriptional regulatory sequences will include a heterologous promoter which is recognized by the host. Conveniently, available expression vectors which include the replication system and transcriptional and translational regulatory sequences together with an insertion site for the CAP18 DNA sequences may be employed. For transformation of mammalian and other eukaryotic cell lines, co-transfection of cell lines in the presence of a suitable marker, such as the DHFR gene may be employed. Transfection may be accomplished using chemical, ballistic, or electroporation techniques.

To be useful in the methods of the present invention, the CAP18 polypeptides are generally obtained in substantially pure form, that is, typically at least about 50% weight/weight (w/w) purity, being substantially free from interfering proteins and contaminants. Preferably the CAP18 polypeptides are isolated or synthesized in a purity of at least about 80% w/w and, more preferably in at least about 95% w/w purity. Using conventional protein purification techniques, homogeneous polypeptide compositions of at least 99% w/w purity can be obtained. For example, the CAP18 proteins may be purified by affinity chromatography using antibodies raised against the CAP18 protein.

The isolated and purified polypeptides of the present invention can be incorporated as components of pharmaceutical compositions useful to attenuate, inhibit, or prevent LPS-associated conditions, such as Gram-negative sepsis, autoimmune disorders, inflammation, and the like. The composition should contain a therapeutic or prophylactic amount of at least one polypeptide according to the present invention present in a pharmaceutically acceptable carrier.

The pharmaceutically acceptable carrier can be any compatible, non-toxic substance suitable to deliver the polypeptide to the patient. Sterile water, alcohol, fats, waxes, and inert solids may be used as the carrier. Pharmaceutically acceptable adjuvants, buffering agents, dispersing agents, and the like, may also be incorporated into the pharmaceutical compositions. Such compositions can contain a single polypeptide or may contain two or more polypeptides according to the present invention to form a "cocktail". The pharmaceutical compositions just described are useful for oral or parenteral administration. Preferably, the compositions will be administered parenterally, i.e. subcutaneously, intravascularly, or intravenously. Alternative modes of administration may also be employed, such as nasal delivery, respiratory delivery, transdermal delivery, and the like.

The concentration of the CAP18 polypeptide in the form of suitable composition can vary widely, i.e., from less than about 0.1% by weight, usually being at least about 1% by weight, to as much as 20% by weight, or more. Specific methods for preparing pharmaceutical compositions are well known in the art and described in more detail in various publications, such as Remington's Pharmaceutical Science, 15th Edition, Mack Publishing Company, Easton, Pa. (1980), which is incorporated herein by reference.

The pharmaceutical CAP18 polypeptide compositions of the present invention can be administered for prophylactic and/or therapeutic treatment of Gram-negative sepsis, autoimmune disorders, and other LPS-related conditions. For therapeutic applications, the pharmaceutical compositions will be administered to a patient already showing signs of the condition, such as septic shock. For prophylactic applications, the polypeptides will be administered to a patient prior to showing signs of septic shock, typically in conjunction with the primary antibiotic treatment for Gram-negative bacterial infection.

The CAP18 polypeptide compositions of the present invention are also useful for detecting the presence of LPS in biological samples, such as patient samples in the diagnosis of Gram-negative sepsis. The isolated and purified CAP18 polypeptides may be utilized as a receptor for LPS in a variety of conventional assay formats, including competitive and non-competitive (sandwich) assay formats; radiometric, enzymatic, colormetric, luminescent, and phosphorescent formats; homogeneous and heterogenous formats, and the like. Generally, such assay formats will rely on competitive or direct binding of the CAP18 molecule to LPS which may be present in the sample, where binding of the native LPS in the sample will be detected. Numerous suitable formats are described in the medical, scientific, and patent literature.

The following examples are offered by way of illustration, not by way of limitation.

EXPERIMENTAL

1. Cloning of Rabbit CAP18

Protein sequence of CAP18—Rabbit CAP18 was purified from rabbit peritoneal exudate cells elicited by IP injection of 500 ml of 0.25% sodium caseinate. Cells were washed and extracted with 0.1M citric acid. The acid soluble fraction was precipitated with 80% ethanol and applied to heparin-sepharose CL-6B column. The tightly bound cationic proteins eluting with 2M NaCl were used for further study. C8 reverse phase HPLC of the heparin bound material yielded two major peaks. The first peak (@26.1 min.) actively inhibited LPS induced tissue factor generation from murine macrophages (Hirata M, et al., unpublished data). The active peak was sequenced using an Applied Biosystems Model 477A protein/peptide sequencer with an on-line Applied Biosystems 120A PTH-amino acid analyzer. The sequence of the first 28 amino acids of the putative N-terminus of CAP18 was: GLY-LEU-ARG-LYS-ARG-LEU-ARG-LYS-PHE-ARG-ASN-LYS-ILE-LYS-GLU-LYS-LEU-LYS-LYS-ILE-GLY-GLN-(ASP or LYS)-ILE-GLN-(GLN or ILE)-(GLY or GLN)-LEU-LEU (SEQ ID NO:7). Searches of the GenBank and the National Protein databases revealed that this sequence is unique. Note that this sequence was later found to correspond to the N-terminus of the C-terminal RNIP fragment of rabbit CAP18 (SEQ ID NO:4, amino acids 135–162).

Construction cDNA library—Rabbit bone marrow cells were harvested and lysed with guanidinium thiocyanate, and spun on a cesium chloride gradient as per Maniatis, T., et al., *"Molecular Cloning: A Laboratory Manual."* (1982) Cold Spring Harbor Laboratory, Cold Spring Harbor, N.Y. Poly (A)+mRNA was selected on an oligi dT-cellulose column (Pharmacia). 5 μg mRNA was used to construct a cDNA library, using the cDNA Synthesis System Plus kit (Amersham). EcoRI restriction sites were methylated, and EcoRI linkers were ligated overnight at room temperature using T4 DNA Ligase (New England Biolabs). Excess linker was digested with EcoRI. The cDNA was size fractionated over a Sepharose S-400 column, ligated into lambda gt10 vector (Lambda Vector Kit, Stratagene). C600Hfl bacteria were infected with the packaged lambda and grown on NZYDT plates. Random plaques were amplified via polymerase chain reaction (PCR) (Perkin Elmer Cetus) using primers made to the Lambda arms flanking the insert site.

Isolation of cDNA clones—A 20 nucleotide, degenerate probe was designed from amino acids #11–17 of the sequence of CAP18 fragment: 5'-AA(CT)AA(GA)AT(CTA)AA(GA)GA(GA)AA(GA)CT (SEQ ID NO:8). The probe was paired with vector derived primers flanking the insert site. Amplified PCR fragments were subcloned into ml3mpl8 phage and pcDNAI plasmids for sequencing by the dideoxy chain termination method Sanger, F., et al., *Proc. Natl. Acad. Sci. (USA)* (1977), 74:5463–5467. Messing, *J. Methods Enzymol.* (1983), 101:20–78. A 200 bp PCR fragment was found to encode the known CAP18 amino acid sequence, some additional 3' information, and a poly A tail. This fragment was used to generate random primed probes as per manufacturer's instructions (Boehringer-Mannheim), and used to screen the library for the full-length cDNA.

Two pairs of oligonucleotide probes were designed corresponding to amino acids #11–17 and #15–21 respectively. Initial attempts using conventional screening failed to identify a positive clone. An alternative approach using PCR was employed. CAP18 oligonucleotide #11–17 was matched with primers designed from the lambda phage arms. A 200 bp fragment corresponding to CAP18 was amplified, purified and used to screen the cDNA library. In the library of 400,000 plaques, greater than 100 clones hybridized to the probe. Twenty of these primary positives were replated and 4 were subcloned into plasmids for sequence analysis.

The cDNA and predicted amino acid sequences of rabbit CAP18 are shown in SEQ ID NO:3 and SEQ ID NO:4, respectively. The rabbit CAP18 cDNA encodes a 29 amino acid signal peptide follow-d by a mature protein of 142 amino acids. The protein is predicted to be 16.6 kDa and to have a pI of 10. No N-linked glycosylation sites are predicted. There are four cysteines. The sequence derived from Edman degradation is found at the carboxy-terminus of the protein beginning at amino acid position 135.

cDNA library screening—Confluent plates were transferred to nitrocellulose filters. The filters were UV-cross-linked (Stratagene, UV Stratalinker) and incubated for 2 hours in 50% formamide, 50% PAM. Filters were hybridized at 42° C. overnight with fresh solution containing the random primed probe. Filters were washed once at room temperature for 15 minutes in 2× SSC, 0.1% SDS; then in 1× SSC, 0.1% SDS; and a third time in 0.5× SSC, 0.1% SDS. Positives were subcloned into m13mp18 and/or pcDNA (Invitrogen) and sequenced.

Computer Analysis of DNA and Protein Sequences—Generation of the predicted amino acid sequence was performed using the DNA Matrix program. Analysis of the primary and secondary structures of the protein based on the DNA sequence was performed using the PCGENE program. Genebank searches at the nucleotide and amino acid levels were conducted using the programs FASTA and TFASTA, Lipman, D. J. and Pearson, W. R. *Science* (1985), 227:1435–1441.

2. Identification of Rabbit RNIP

Figure 2:
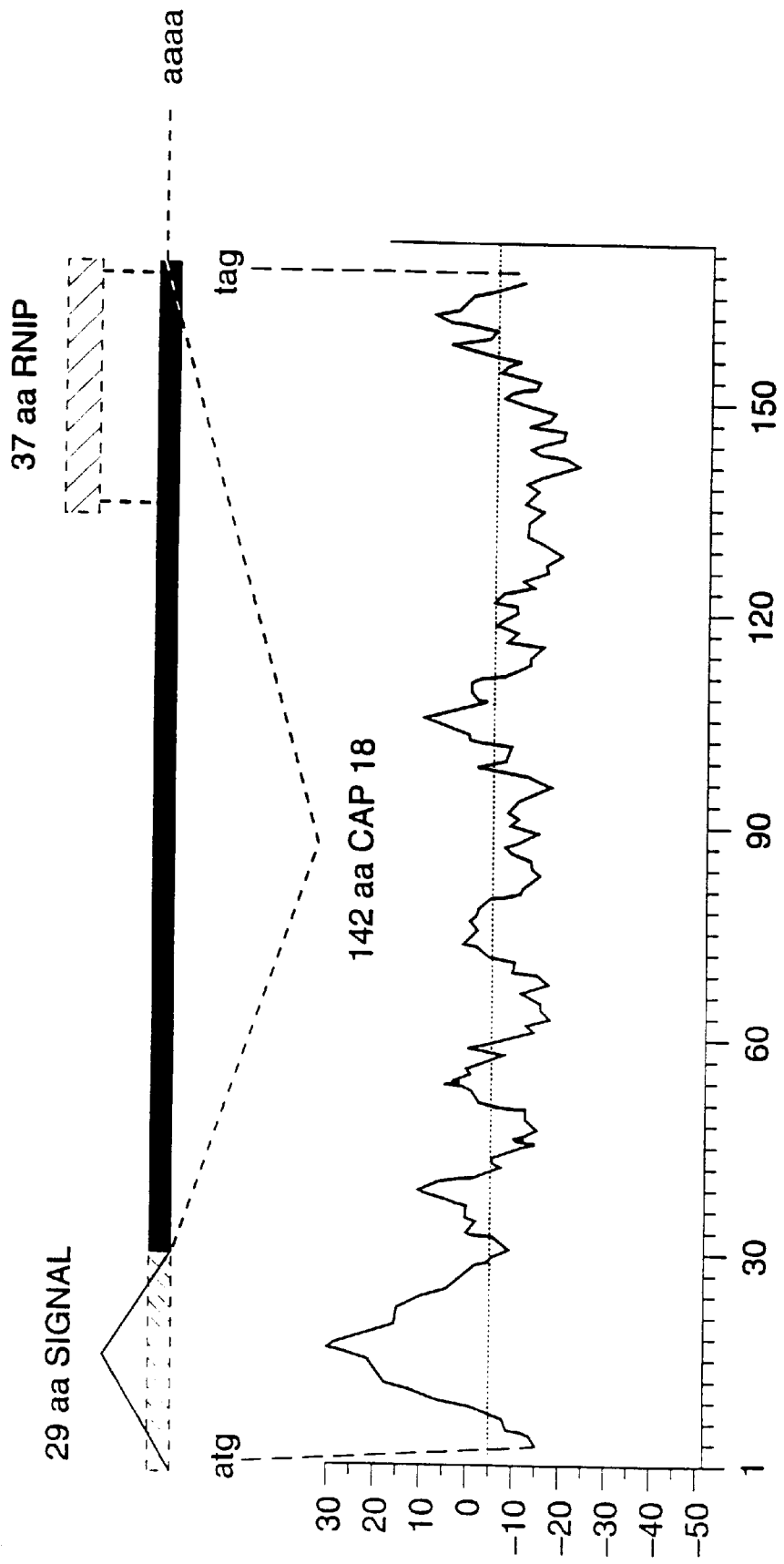
FIG. 2 is the hydropathic profile of CAP18 based on the amino acid sequence derived from DNA SEQ:1. The 29 amino acid amino-terminal signal sequence and 37 amino acid carboxy-terminal reactive nitrogen inhibitory protein (RNIP) are shown.
Figure 3:
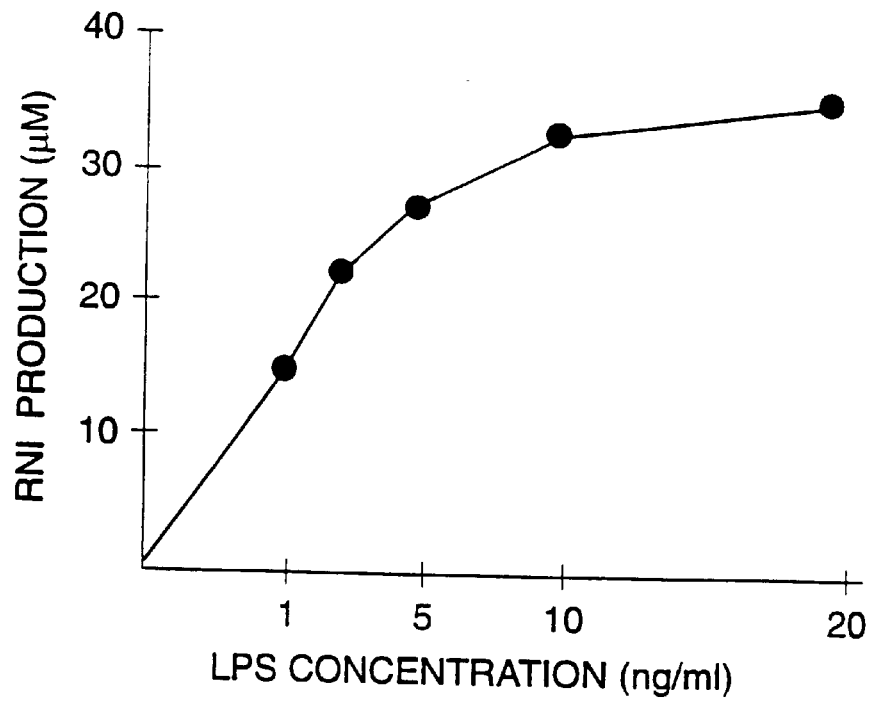
FIG. 3 is a graph illustrating the dose response of lipopolysaccharide (LPS)-induced reactive nitrogen intermediate (RNI) production, as described in the Experimental section.

From the sequence of the CAP18 cDNA, it was apparent that the putative N-terminal peptide of CAP18 was in fact an internal fragment of the CAP18 protein. We therefore tried to reconfirm the original protein sequence. Neutrophil-derived heparin bound cationic proteins were prepared as described above and applied to a C18 reverse phase HPLC (FIG. 1). We sequenced the major peaks. Peaks at fractions 14.5 and 15.2 correspond to defensins MCP1 and MCP2 (Territo et al. (1989) J. Clin. Invest. 84:2017–2019), respectively. Fraction 25.8 is macrophage related protein 14 (MRP14) (Odink et al. (1987) Nature 330:80–82). The fraction at 20.3 minutes corresponds to a fragment of CAP18 of approximately 4–5 kD. This fragment was shown to inhibit LPS-induced reactive nitrogen intermediate (RNI) production and was named reactive nitrogen inhibitory protein (RNIP) (FIG. 2). FIG. 3 demonstrates a dose response of LPS induced RNI production by cultured murine macrophage cell line (RAW 264.7). The murine macrophage cell line RAW 264.7 (obtained from ATCC) and thioglycollate-elicited murine peritoneal exudate cells are used to produce RNI. Cells are cultured at $1\times10^6$/ml. in RPMI-1640 +2.5% FCS in 24 well plates in the presence or absence of different concentrations of LPS or murine rIFNγ. After 24 hr. incubation at 37° C., the cell free supernatant is collected and tested for the presence of RNI. Accumulation of nitrite in the medium is measured by a calorimetric assay based on the Griess reaction (Green et al. (1982) Anal. Biochem. 126:11) using sodium nitrite as standards. Sample (50 μl) is mixed with 50 μl of Griess reagent (1% sulfanilamide, 0.1% naphthalene diamine dihydrochloride, 2.5% $H_3PO_4$) and after 10 min. at room temperature absorbance is read at 570 nm.

Figure 4:
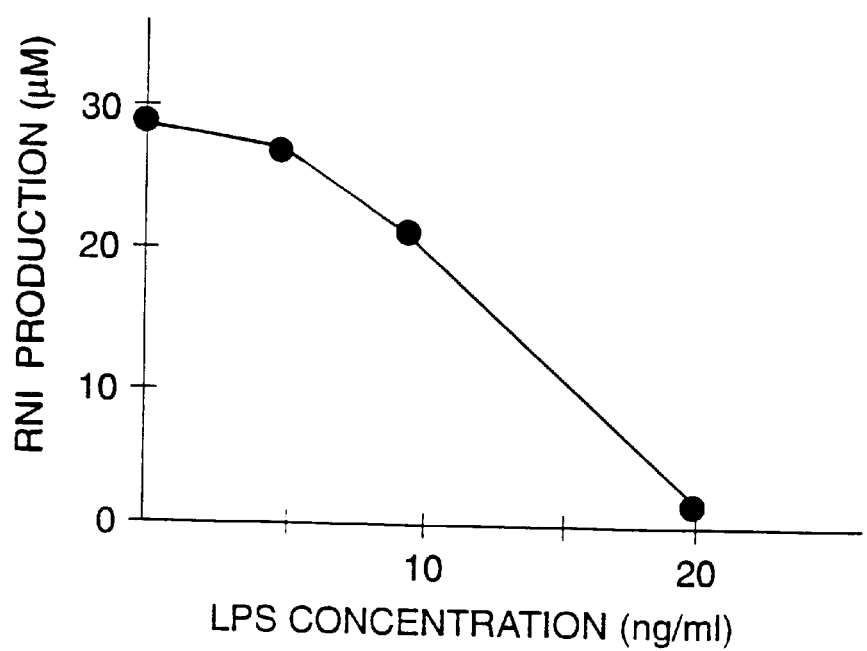
FIG. 4 is a graph illustrating the inhibition of LPS-induced RNI production by polymyxin B, as described in the Experimental section.

FIG. 4 demonstrates inhibition of LPS [5 ng/ml]-induced RNI production in RAW 264.7 cells by polymyxin B, a stoichiometric inhibitor of LPS. Such inhibition serves as a positive control for the induction of RNI activity hereinafter.

Figure 5:
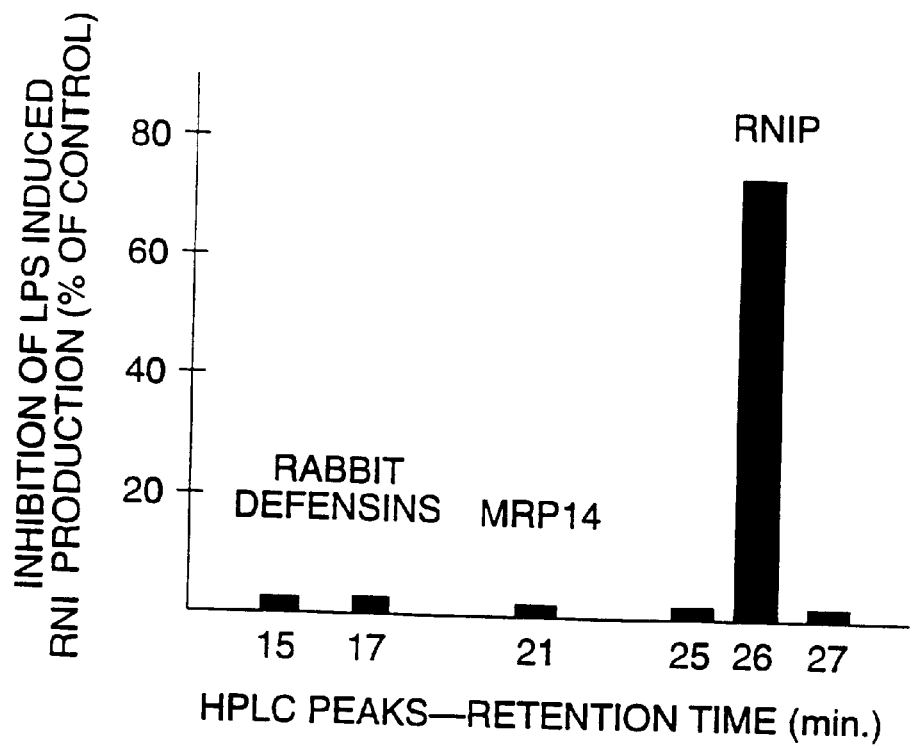
FIG. 5 is a graph illustrating the activity of RNIP relative to certain other mammalian cationic proteins in inhibition of LPS-induced RNI production, as described in the Experimental section.

We tested the anti-LPS activity of the HPLC-purified rabbit peptides shown as peaks in FIG. 1. We measured their capacity to inhibit LPS-stimulated nitrogen radical release from macrophages. FIG. 5 shows that only the peak corresponding to RNIP was active. RNIP inhibits RNI release from thioqlycollate-elicited murine PECs stimulated by IFNγ alone or the synergistic combination of IFNγ plus LPS (Table 1). Subsequently we showed that the $IC_{50}$ for inhibition of gamma interferon stimulated nitrogen radical release by RNIP was less than 50 nM (Table 2).

Furthermore RNIP inhibits both LPS and IFNγ induced TNF release (Table 3) from human macrophages. Thus, RNIP is a novel peptide derived from an LPS binding protein that acts directly on macrophages to attenuate their activation by diverse stimuli.

TABLE 1

RNIP blocks LPS and IFN$_\gamma$ induced generation of nitrogen radicals from Raw 264.7 cells

| | Stimulus alone | RNIP (1:1) | RNIP (1:10) | RNIP (1:100) |
|---|---|---|---|---|
| Unstimulated | 2.2* | — | — | — |
| LPS (2.5 ng/ml) | 27 | 4 | 16 | 24 |
| Murine IFN$_\gamma$ (250 U) | 30 | 15 | 18 | 20 |

*$\mu$M reactive nitrogen intermediates (RNI).

TABLE 2

RNIP blocks synergistic action of LPB and IFN$_\gamma$ induced generation of nitrogen radicals from day 3 thioglycolate (4%/1 ml) elicted murine peritoneal exudate cells

| Stimulus | Concentration | RNIP | RNI ($\mu$M)* |
|---|---|---|---|
| LPS | 1 ng/ml | — | 0 |
| | 100 ng/ml | — | 1.7 ± 0.4 |
| IFN$_\gamma$ | 5 U/ml | — | 0 |
| | 50 U/ml | — | 0.7 ± 0.6 |
| | 500 U/ml | — | 4.0 ± 0.8 |
| | 1000 U/ml | — | 7.0 ± 0.8 |
| IFN$\mu$ | 500 U/ml | 50 nm | 1.1 |
| LPS + IFN$_\gamma$ | 1 ng + 500 U/ml | — | 26 ± 0.6 |
| LPS + IFN$_\gamma$ | 1 ng + 500 U/ml | 50 nm | 14 ± 0.7 |

*reactive nitrogen intermediate

TABLE 3

RNIP blocks TNF release from LPS and IFN$_\gamma$ stimulated human monocytes

| | Stimulus alone | CAP Buffer | CAP (1:1) | CAP (1:10) | CAP (1:100) |
|---|---|---|---|---|---|
| Control | 0.04* | 0.06 | — | — | — |
| LPS (10 ng/ml) | 1.0 | 1.2 | 0.12 | 0.34 | 0.23 |
| Human IFN$_\gamma$ (100 U) | | 2.0 | 2.2 | 0.27 | 0.35 |
| 0.35 | | | | | |

*ng/ml TNF.

In summary, we have purified and protein sequenced a portion of a rabbit anti-LPS protein designated CAP18. From this sequence we have cloned a cDNA corresponding to CAP18. Apparently during the purification process a piece of CAP18 is proteolytically cleaved. This fragment designated RNIP can inhibit release of nitrogen radicals and cytokines by LPS and IFNγ activated macrophages.

3. Synthetic Rabbit RNIP Peptides

All of the data presented above were obtained with RNIP purified from rabbit granulocytes. It was therefore of interest to determine if synthetic RNIP retained similar or identical activities. Furthermore it was of interest to determine if a small fragment of RNIP might bind to LPS and inhibit LPS activation of macrophages.

Synthetic rabbit RNIP and a series of rabbit RNIP-derived fragments were generated based on the sequence of SEQ ID NO:4. These fragments were made using automated solid phase synthesis (Merrifield synthesis) according to standard procedures. Each fragment was purified by HPLC. Table 4 lists the peptide fragments and their activity in LPS hemagglutination assays and inhibition of LPS-induced release of reactive nitrogen intermediate (RNI) radicals.

For hemagglutination assays, erythrocytes were sensitized with LPS as follows. One ml of 1% erythrocyte suspension (human 0 type, C3H/HeN mouse or sheep) was mixed with 0.2 ml of LPS solution and incubated at 37° C. for 30 min, followed by washing with phosphate buffered saline (PBS), and then the concentration of suspension was adjusted to 1.0%. In the case of S-LPS, the solution was heated at 100° C. for 1 hour before sensitization of erythrocytes. Fifty $\mu$l of 1.0% erythrocyte suspension sensitized with LPS was mixed with 50 $\mu$l of a 2-fold serial dilution of CAP in a microtiter U-plate and incubated at 37° C. for 1 hour. Activity of CAP was expressed as a minimum agglutinating concentration (MAC) of CAP. According to the method of Kirikae et al. (1986) Microbiol. Immunol. 30:269–274, 50 $\mu$l of 2-fold serial dilution of Re-LPS was added to 50 $\mu$l of 1.0% rabbit erythrocyte suspension, and incubated at 37° C. for 3 hour. Minimum agglutinating concentration of Re-LPS was expressed as 1 HA unit.

Figure 6A:
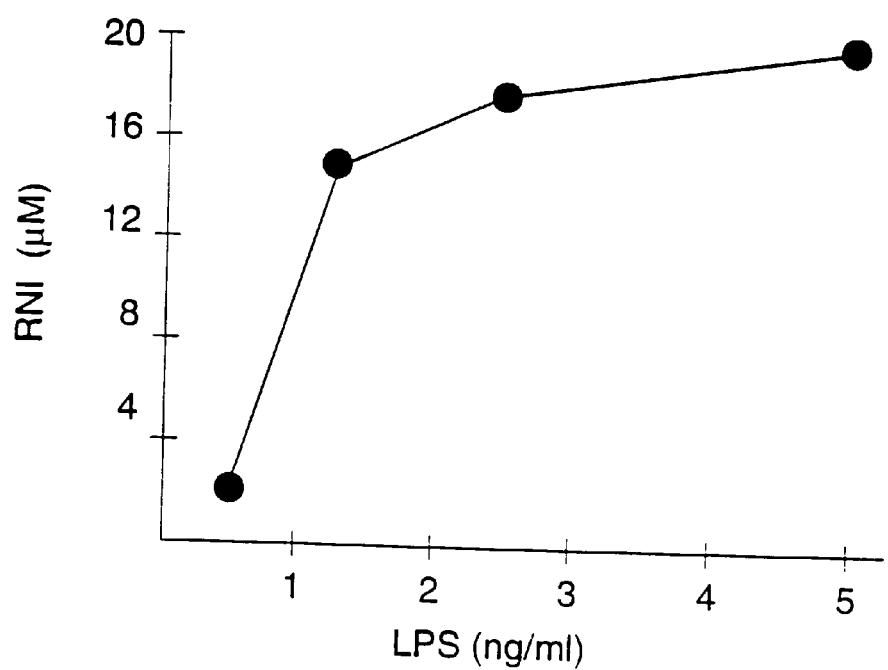
FIG. 6A is a graph illustrating RNI production in RAW 264.7 cells as a function of LPS concentration.
Figure 6B:
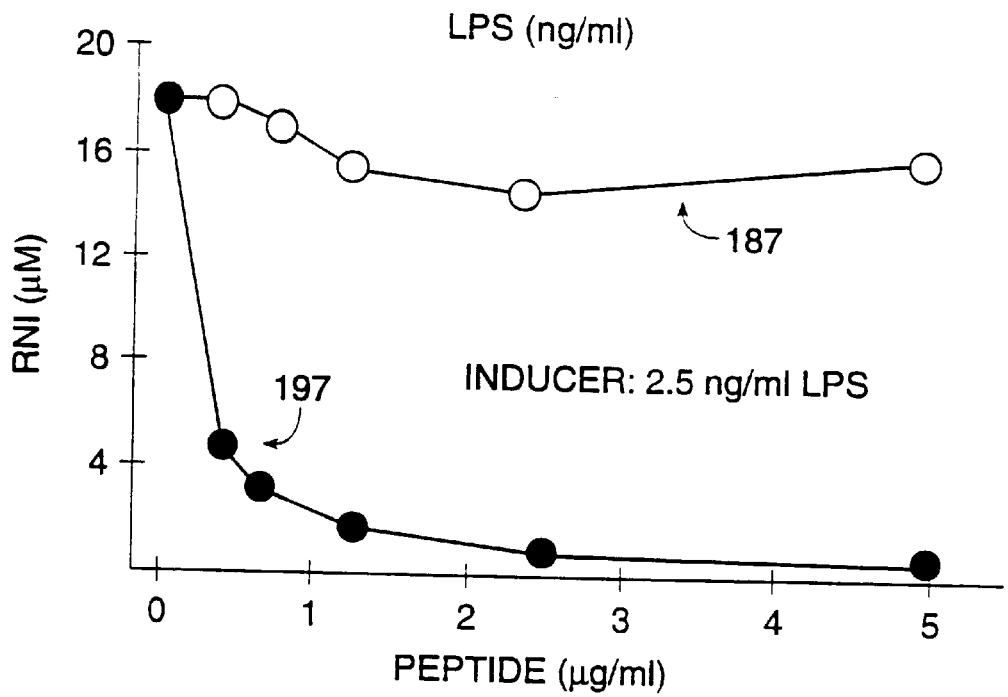
FIG. 6B is a graph illustrating the inhibitory effects of various concentrations of peptides #197 (RNIP) and #187 on RNI production in RAW 264.7 cells induced with 2.5 ng/ml LPS.

The results of these experiments demonstrate that peptide fragment #36-1 and the native RNIP fragment (#197) are active. Other fragments have much less activity. While there is some day-to-day variation in the bioassay, these peptides are active at concentrations of 10–50 nM. FIGS. 6A and 6B compare the dose response of active synthetic RNIP (#197) with an inactive fragment (#187) in inhibition of LPS-induced reactive nitrogen intermediate (RNI) production in RAW 264.7 cells. FIG. 6A shows RNI production in the absence of inhibition, while FIG. 6B compares the inhibitory effects of peptides #197 (RNIP) and #187. The 50% inhibitory concentration (IC$_{50}$) of RNIP in this assay is seen to be about 0.2 $\mu$g/ml (approximately 30 nM).

TABLE 4

RNIP peptide sequences

| | Peptide Charateristics | | | Peptide activity | |
|---|---|---|---|---|---|
| Peptide Code No. | Peptide Sequence † | Molecular Weight | Hemagglutination [MAC ($\mu$g/ml)]* | LPS-induced RNI-IC50 ($\mu$g/ml) | |
| 197/RNIP | 135–171 | 6144 | 7.9 | 0.2 | |
| 187 | 151–171 | 3065 | >125 | >10 | |
| 32-1 | 135–143 | 1857 | >125 | >2 | |
| 21-1 | 135–151 | 3322 | >125 | >2 | |
| 34-1 | 140–166 | 4443 | >125 | >2 | |
| 36-1 | 135–166 | 5396 | 3.9 | 0.08 | |
| 50-1 | 147–171 | 3792 | >125 | 0.3 | |
| 50-2 | 147–171 | 3792 | >125 | 0.3 | |
| 52-1 | 143–169 | 4287 | >125 | >2 | |
| 52-2 | 143–170 | 4402 | >125 | >2 | |
| 52-3 | 132–171 | 4565 | >125 | >2 | |
| 54-1 | 139–170 | 5298 | >125 | >2 | |
| 54-2 | 139–171 | 5461 | >125 | >2 | |

†Based on numbering in SEQ ID NO:4
*MAC = minimum agglutinating concentration of *Salmonella minnesota* Re-LPS sensitized sheep erythrocytes.
+RNI = reactive nitrogen intermediates.

Another series of experiments was performed to determine if the #36-1 and #197 (RNIP) peptides were capable of binding to LPS from various species of Gram-negative bacteria. See Table 5. For these experiments, sheep red blood cells were sensitized with *Salmonella minnesota* Re-LPS. Peptides #36-1 and #197 (RNIP) were preincubated with various preparations of LPS. Both peptides bind to a diverse group of lipopolysaccharides.

TABLE 5

Inhibition of RNIP-mediated hemagglutination by various preparations of lipopolysaccharide

| LPS preparation | Peptide #36-1 MIC*(μg/ml) | RNIP (#197) MIC* (μg/ml) |
|---|---|---|
| Salmonella minnesota R595 | 15.6 | 62.5 |
| E. coli J5 | 7.8 | 15.6 |
| E. coli 0111:B4 | 15.6 | 31.3 |
| E. coli 055:B5 | 15.6 | 62.5 |
| E. coli 0127:B8 | 15.6 | 62.5 |
| Pseudomonas aeruginosa F-D Type I | 3.9 | 15.6 |
| Klebsiella pneumoniae | 31.3 | 62.5 |

*MIC = minimal inhibitory concentration of LPS.
+Peptide #36-1 (16 μg/ml) and RNIP (#197) (25 μg/ml) were preincubated with each LPS preparation at 37° for 30 minutes, and each reaction mixture was added to sheep erythrocytes sensitized with Re-LPS.

Further antibacterial assays were performed on the following bacterial strains: Salmonella typhimurium LT2(S), S. minnesota R595 (Re), E. coli O9:K39 (K+, K−), E. coli O111:1B4, Pseudomonas aeruginosa, Klebsiella pneumoniae, Staphylococcus aureus (methicillin sensitive=MSSA and resistant=MRSA) and Candida albicans were used. The latter 5 strains were clinical isolates.

All strains were grown in Tryptosoy broth (Eiken Co., Tokyo, JAPAN). Salmonella typhimurium LT2(S), S. minnesota R595(Re), E. coli O9:K39(K+, K−) E. coli O111:B4 and Klebsiella pneumoniae were plated on Nutrient agar (Eiken Co.). Pseudomonas aeruginosa and Candida albicans were plated on NAC agar and GS (Guanofracin-Sabouraud) agar plates, respectively. Bacterial cultures were collected at logarithmic phase and washed twice with phosphate-buffered saline pH 7.2, and adjusted to a final concentration of $5 \times 10^3$–$1 \times 10^4$ cells/ml. To 450 μl of bacterial suspension, 50 μl of peptide was added and incubated at 37° C. for 1 hour, and 100 μl of the reaction mixture was plated on the agar plate. After 24 hr-incubation at 37° C., colony-forming units (CFU) were counted. As a control experiment, PBS was added to bacterial suspension and incubated for 1 hour, plated on agar, and cultured. For some experiments the percent of control CFU was determined. Bacteria were grown in trypticase broth overnight. The following day, bacteria were suspended at $10^5$/ml in RPMI with 10% fetal calf serum. The assay was set up in a 96 well plate containing 50 μl bacteria plus 50 μl peptides and incubated at 37° C. for 1 hr, then 1 μCi $^3$H-thymidine (Amersham) is added to each well and incubated with the bacteria overnight. The assay is terminated by addition of 10% TCA and harvested and counted on a Matrix 96 Packard beta counter.

Figure 6C:
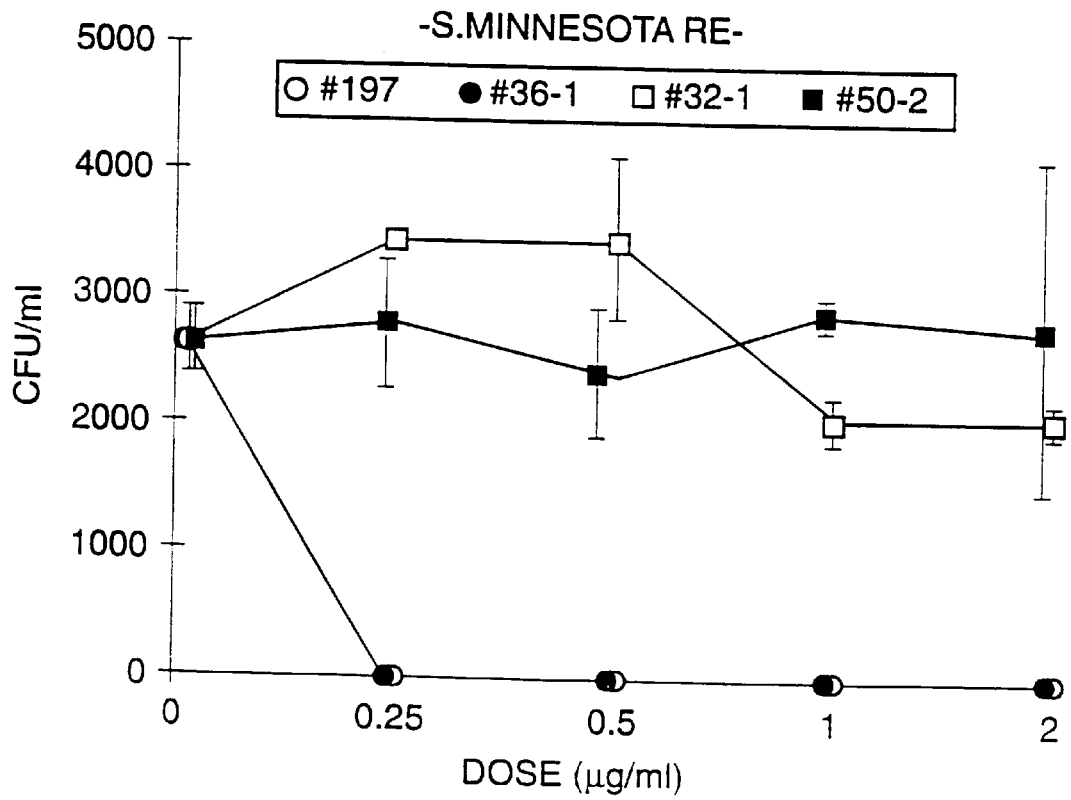
FIGS. 6C–6E show the antibacterial activity of four synthetic RNIP peptides against various bacterial strains.

Antibacterial activity of peptides 197 (rabbit RNIP), 36-1, 32-1, and 50-2 were measured on the rough mutant strain, Salmonella minnesota Re. FIG. 6C presents a dose-response of the four peptides on Salmonella Minnesota Re CFU. Non-LPS binding peptides 32-1 and 50-2 are not active whereas LPS-binding peptides, 97 and 36-1 have significant anti-bacterial activity ($IC_{50}$<100 ng/ml; 40 nM).

Figure 6D:
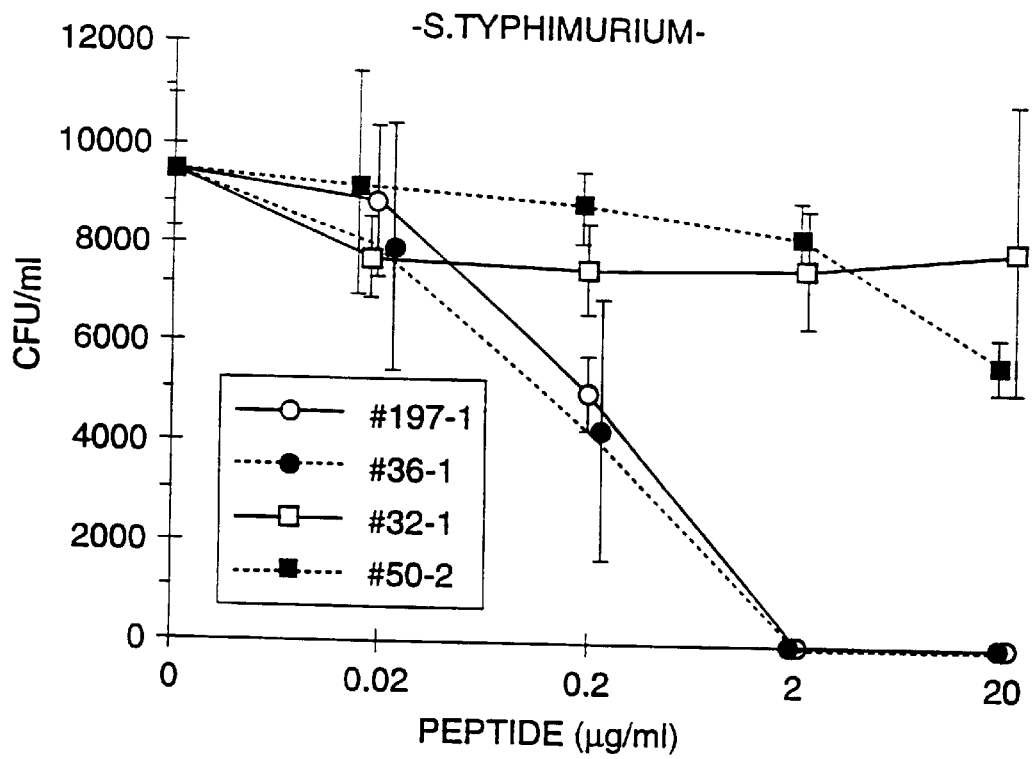
Figure 6E:
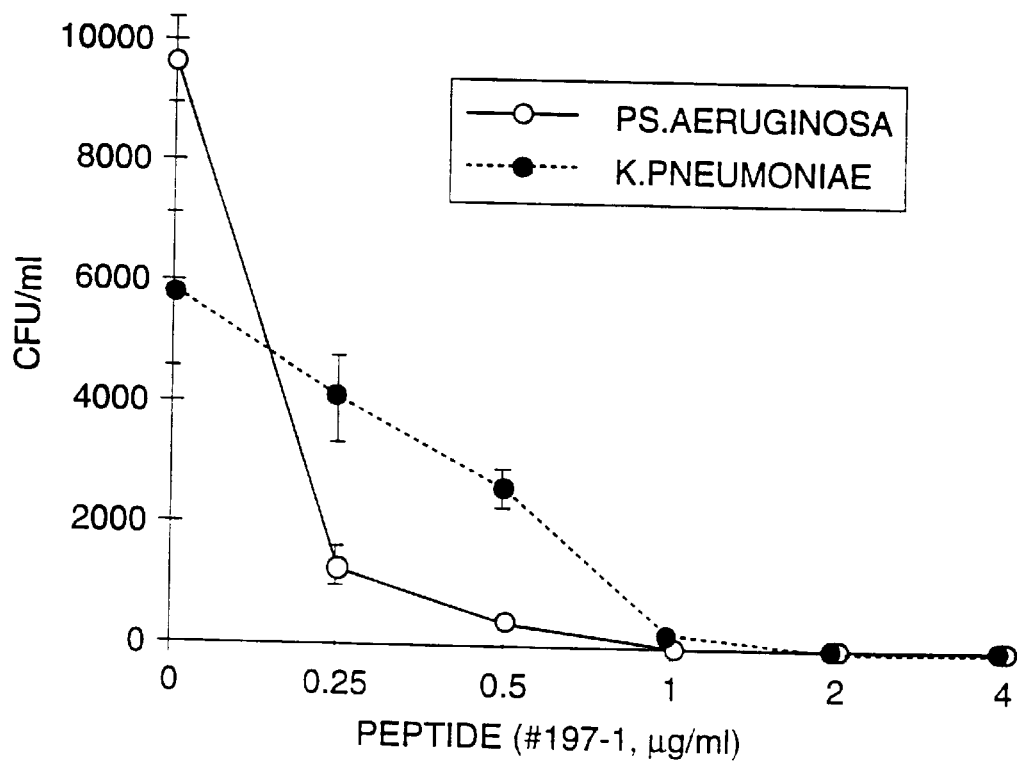

Next the activity versus a smooth enterobacterial strain, Salmonella typhimurium was tested (FIG. 6D). Non-LPS binding peptide 32-1 and 50-2 are not active whereas LPS-binding peptides, 197 and 36-1 have significant anti-bacterial activity ($IC_{50}$=220–280 nM). FIG. 6E demonstrates that peptide 197 has significant activity versus two other clinical strains of bacteria, Pseudomonas aeruginosa ($IC_{50}$<250 μg/ml; 40 nM) and Klebsiella pneumoniae ($IC_{50}$<440 ng/ml; 70 nM). Similar results were obtained when peptide 36-1 was tested versus Pseudomonas aeruginosa ($IC_{50}$<250 ng/ml; 50 nM) and Klebsiella pneumoniae ($IC_{50}$<540 ng/ml; 100 nM) (graphs not shown).

Figure 6F:
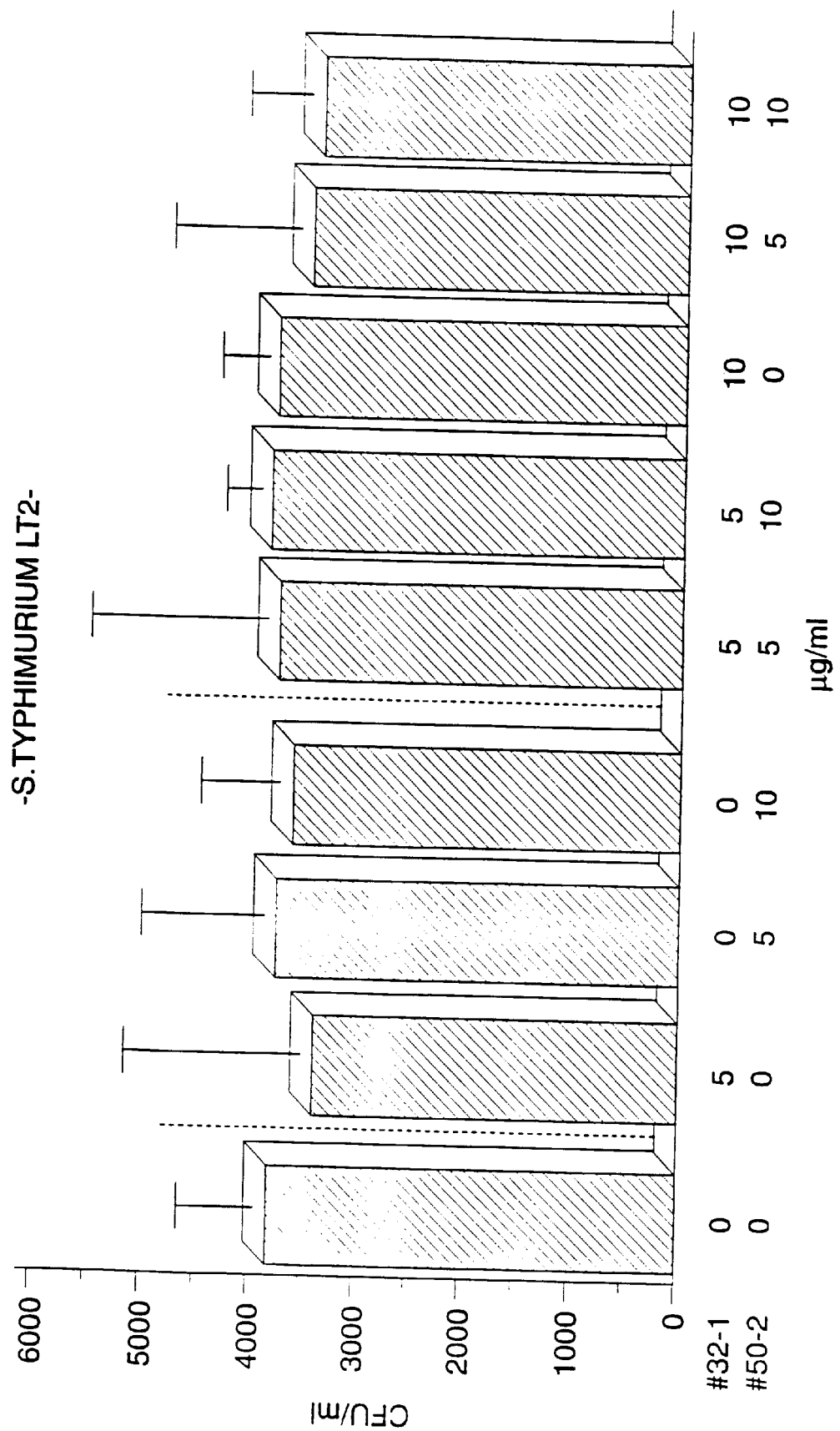
FIG. 6F shows the antibacterial activity of synthetic RNIP peptides which do not exhibit LPS binding activity.
Figure 6G:
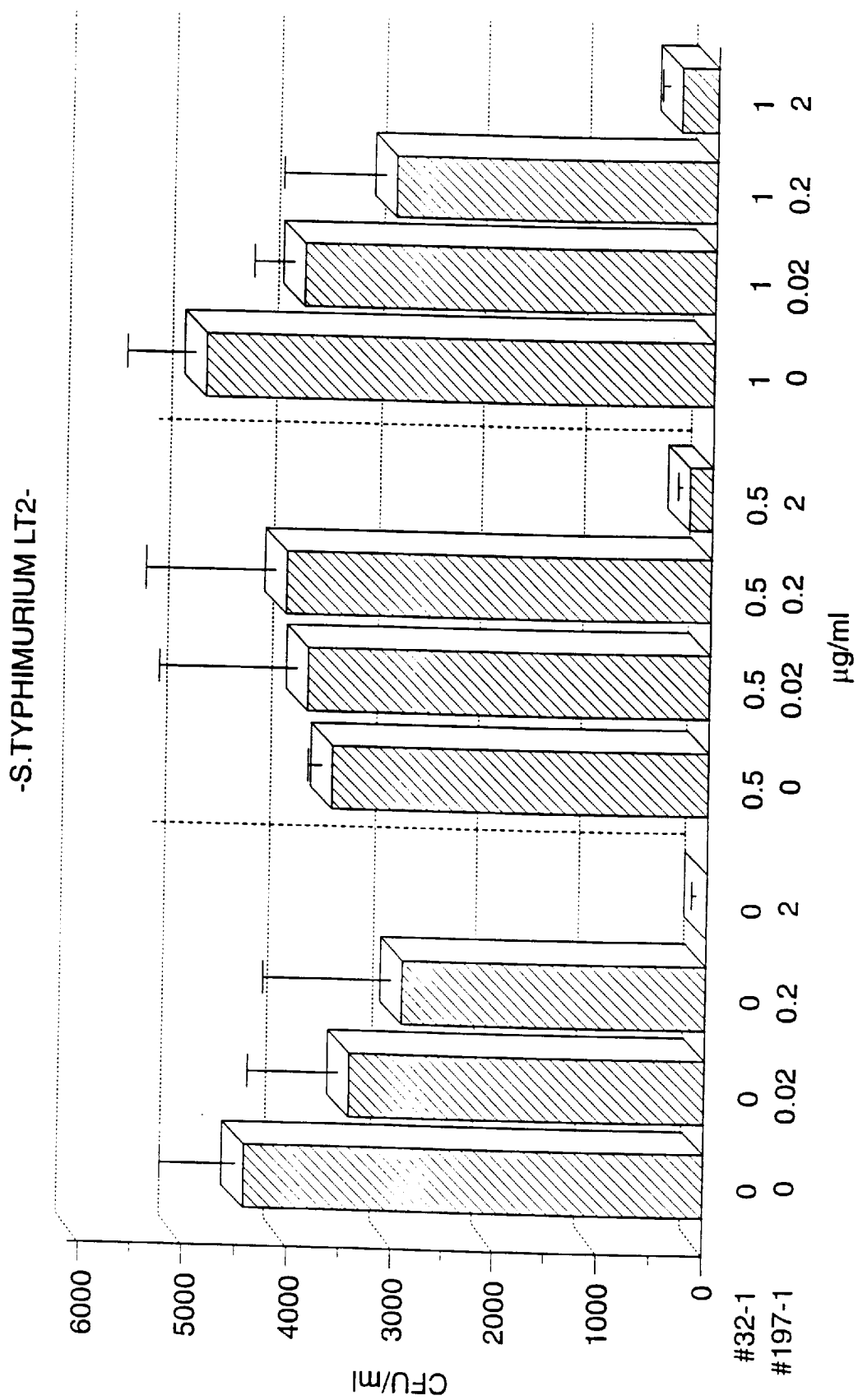
FIG. 6G shows that peptide 32-1, which does not bind LPS, also does not inhibit the activity of RNIP peptide 197.

Two other control experiments were carried out with the non-LPS binding peptides. In the first case (FIG. 6F), peptides 32-1 and 50-2 were added at high concentrations alone and in various combinations to determine their effects on the CFU of S. typhimurium. No effect was observed. In the second case, S. typhimurium was pretreated with peptide 32-1 and subsequently exposed to peptide 197 (FIG. 6G). In this case no inhibition or augmentation of bacterial killing by peptide 197 was observed. These experiments in conjunction with those carried out above demonstrate that the inhibitory effect of peptide 197 (RNIP) has specific structural requirements.

To corroborate the anti-bacterial activity shown in the CFU assays, inhibition of proliferation of bacteria was tested directly using a $^3$H-thymidine incorporation assay. This assay also addresses any artifacts resulting from clumping of the test strains mediated by RNIP peptides that would falsely inhibit a CFU type of assay. The results of shown in Table 5A demonstrate that RNIP inhibits the proliferation of E. coli, Klebsiella pneumoniae, and two strains Pseudomonas spp. In summary although there is some strain to strain variation in the $IC_{50}$, all of the Gram-negative strains tested in two different types of assays were sensitive to these anti-microbial peptides.

TABLE 5A

RNIP inhibits bacterial proliferation*

| | Concentration of RNIP (μg/ml) | | | |
|---|---|---|---|---|
| Strain | 5.0 | 2.5 | 1.25 | 0.6 |
| A. Gram-negative bacteria | | | | |
| E. coli (HB101) | 99 | 99 | 88 | 81 |
| Klebsiella pneumoniae | 60 | 17 | 14 | 4 |
| Pseudomonas aeruginosa | 99 | 96 | 82 | 75 |
| Pseudomonas apacia | 99 | 99 | 80 | 81 |
| B. Gram-positive bacteria | | | | |
| Streptococcus pneumoniae | 93 | 68 | 47 | 31 |
| Streptococcus pyogenes | 96 | 90 | 79 | 74 |
| Staphylococcus aureus, coagulase positive | 83 | 72 | 57 | 23 |

*Percent inhibition of proliferation; results are representative of 3 experiments.

Figure 6H:
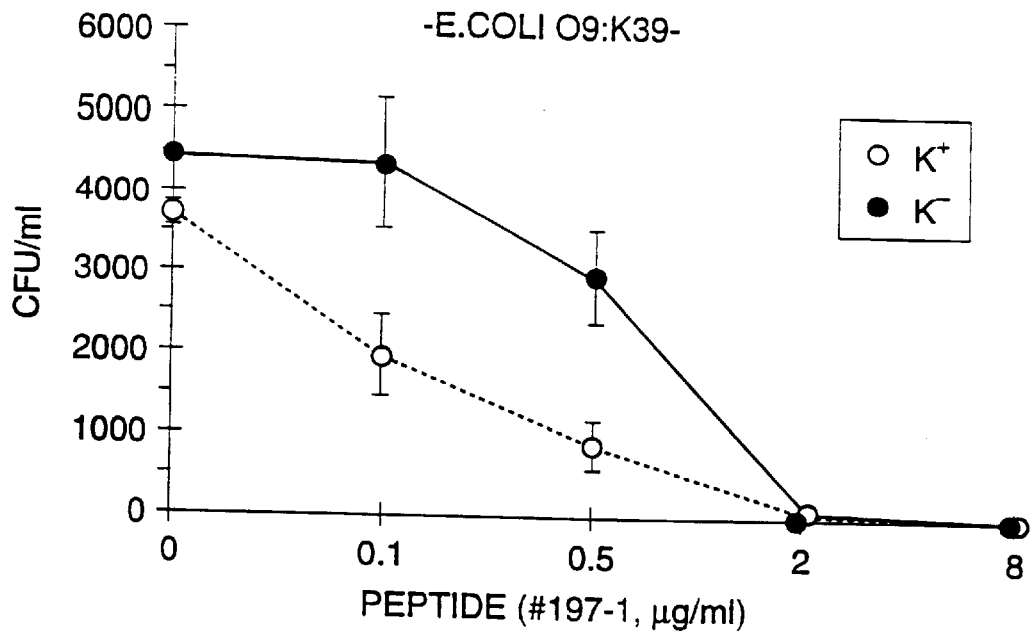
FIG. 6H shows the antibacterial activity of RNIP against $K^+$ and $K^-$ strains of E. coli.

Further studies examined the of sensitivity of encapsulated strains was examined. FIG. 6H compares the activity of peptide 197 versus encapsulated and non-encapsulated E. coli O9:K39. The K− strain is less sensitive to the peptide ($IC_{50}$=680 ng/ml; 110 nM) than the K+ strain ($IC_{50}$=140 ng/ml; 20 nM).

Finally the effect of serum on killing was studied because other anti-microbial peptides require non-physiological conditions (e.g. hypotonic buffers and acidic pH 5.0–5.5) to exhibit activity. Table 5B demonstrates that addition of fetal calf serum to the proliferation assay performed in RPMI-1640 results in only a modest decrease in anti-bacterial activity.

TABLE 5B

RNIP (2.5 μg/ml) inhibits *E. coli* (HB101)
proliferation in the presence of FCS

| FCS concentration (%) | Inhibition (%) |
|---|---|
| 0 | 94 ± 10.3 |
| 1 | 91 ± 10.9 |
| 5 | 87 ± 3.1 |
| 10 | 78 ± 5.5 |

Figure 6I:
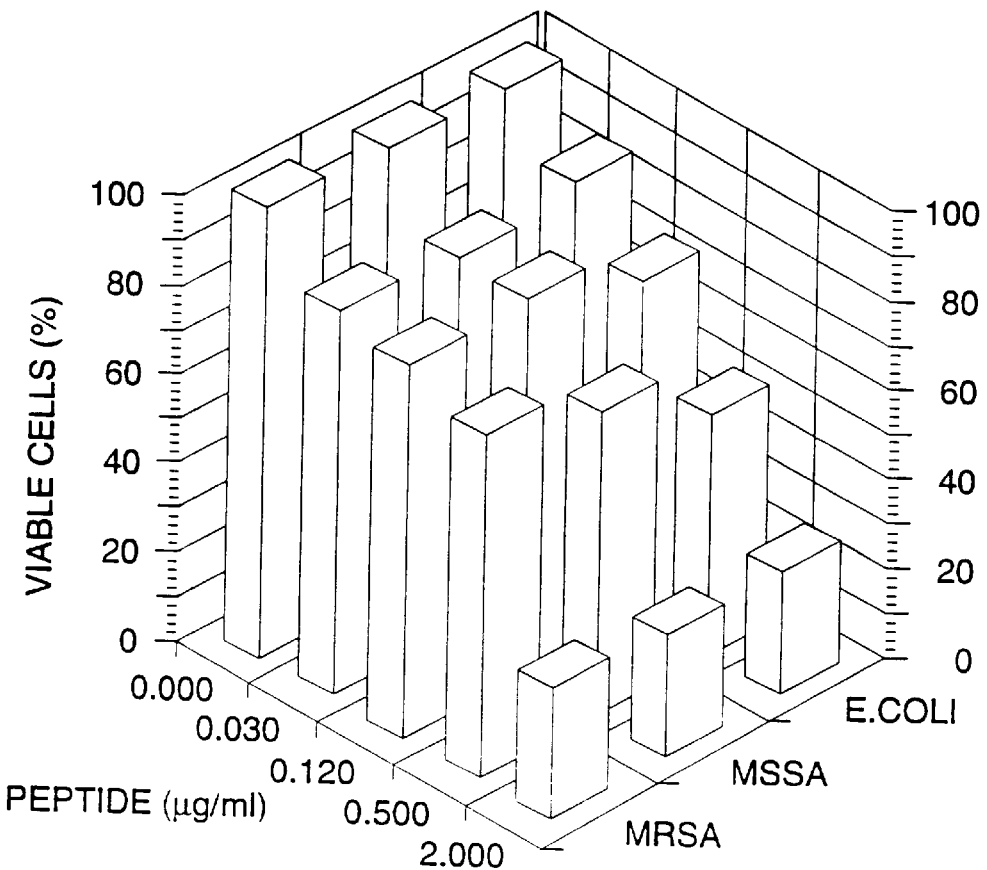
FIG. 6I shows the antibacterial dose response of RNIP peptide 197 against both Gram-negative and Gram-positive bacteria.

Table 5A demonstrates that peptide, 36-1 inhibits proliferation of several Gram positive bacterial strains including *Streptococcus pneumoniae, Streptococcus pyogenes,* and coagulase-positive *Staphylococcus aureus.* To corroborate the proliferation assay peptide 36-1 was next shown to inhibit CFU of both methicillin-sensitive ($IC_{50}$=580 ng/ml; 110 nM) and methicillin-resistant ($IC_{50}$=720 ng/ml; 130 nM) *Staphylococcus aureus* (data not shown). FIG. 6I confirms the anti-Gram positive activity comparing the activity of peptide 197 versus both methicillin-sensitive ($IC_{50}$=940 ng/ml; 150 nM) and methicillin-resistant ($IC_{50}$=1000 ng/ml; 160 nM) *Staphylococcus aureus* with its activty versus *E. coli* ($IC_{50}$=500 ng/ml; 80 nM).

The highly active anti-bacterial peptides 197 and 36-1 were inactive over the range 0–20 μg/ml versus *Candida albicans* (data not shown) and versus multiple drug-resistant *Mycobacterium tuberculosis* and two strains of *Mycobacterium avium* (data not shown).

These data have shown that the C-terminus but not the N-terminus of the rabbit CAP18 protein could be truncated with out loss of activity. The two best LPS binding peptides, 197 (RNIP) and 36-1, have potent (submicromolar) anti-bacterial activity versus all Gram negative strains tested and against many Gram positive strains. Furthermore activity was demonstrated in the presence of serum at neutral pH in a physiological medium. No activity was demonstrated for *Candida albicans* or two Mycobacterial strains.

The activity of CAP18 is to be contrasted with that of BPI which was originally shown to have anti-bacterial activity versus a variety of Gram-negative bacteria, with no activity versus Gram-positive or fungal organisms. Both the amino-terminal fragment ($rBPI_{23}$) and the holoprotein ($BPI_{55}$) exhibited growth inhibitory activity (about 100-fold reduction over control) against an encapsulated *E. coli.* While both $BPI_{55}$ and $rBPI_{23}$ inhibited the growth of a rough mutant strain of *Proteus mirabilis,* only the $rBPI_{23}$ inhibited growth of the wild-type smooth organism. Neither $rBPI_{23}$ nor holoprotein $BPI_{55}$ demonstrated inhibition of Gram-positive *Staphylococcus aureus* (Weiss et al. (1992) J. Clin. Invest. 90:1122–1130).

Three other families of granulocyte proteins exhibit LPS binding and anti-microbial activity. These include the 13 amino acid C-terminal peptide of bovine indolicidin, the 30–35 amino acid family of defensins and azurocidin (CAP37). The indolicidin peptide and the defensins only inhibit the growth of Gram-positive and Gram-negative bacteria in hypotonic media, thus distinguishing them from RNIP. A recent publication describes peptides derived from CAP37 which are active at a concentration approximate 2–3 logs higher than those derived from CAP18.

4. Cellular Receptors for Rabbit RNIP

Figure 7:
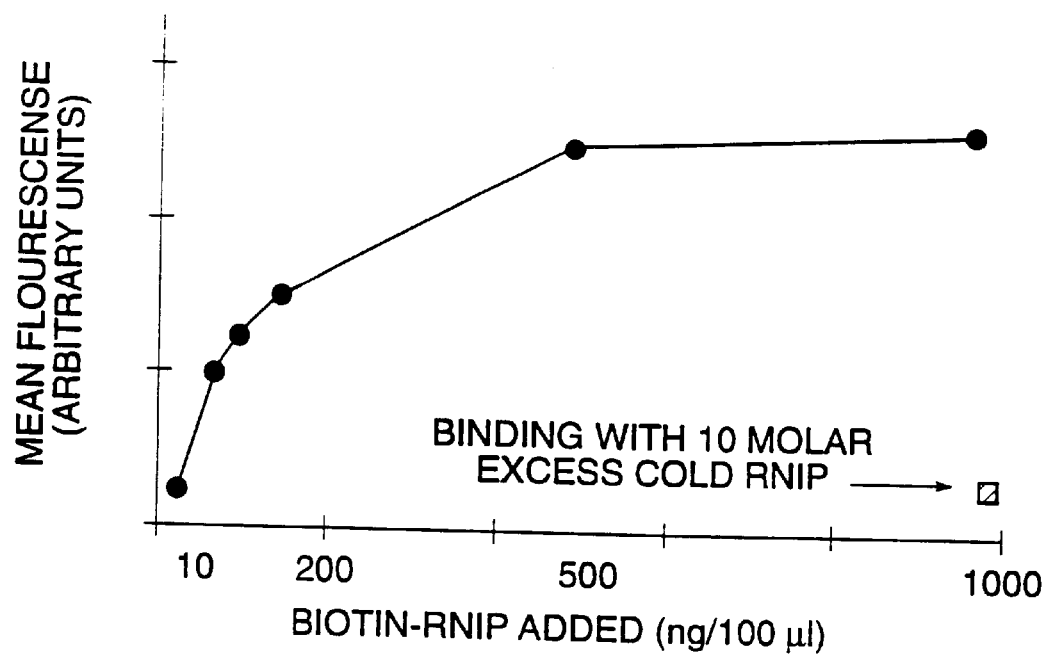
FIG. 7 is a graph illustrating the binding of biotin-labeled RNIP to RAW 264.7 murine macrophage cells.

RNIP was prepared with a biotin group attached to a lysine residue. This biotin-RNIP was shown to be bioactive in an RNI assay (i.e., biotinylation did not alter activity of the molecule). RAW 264.7 cells were washed free of culture medium, and binding of the biotinylated RNIP was carried out at 4° C. in Iscove's OMEM supplemented with 1% fetal calf serum. Cells were then washed free of excess biotin-RNIP, and streptavidin-phycoerythrin (PE) was added. Binding of biotin-RNIP to the cells was assessed using flow cytometry. The results are shown in FIG. 7.

5. RNIP reverses LPS-induced Inhibition of RAW 264.7 Cell Proliferation

Figure 8:
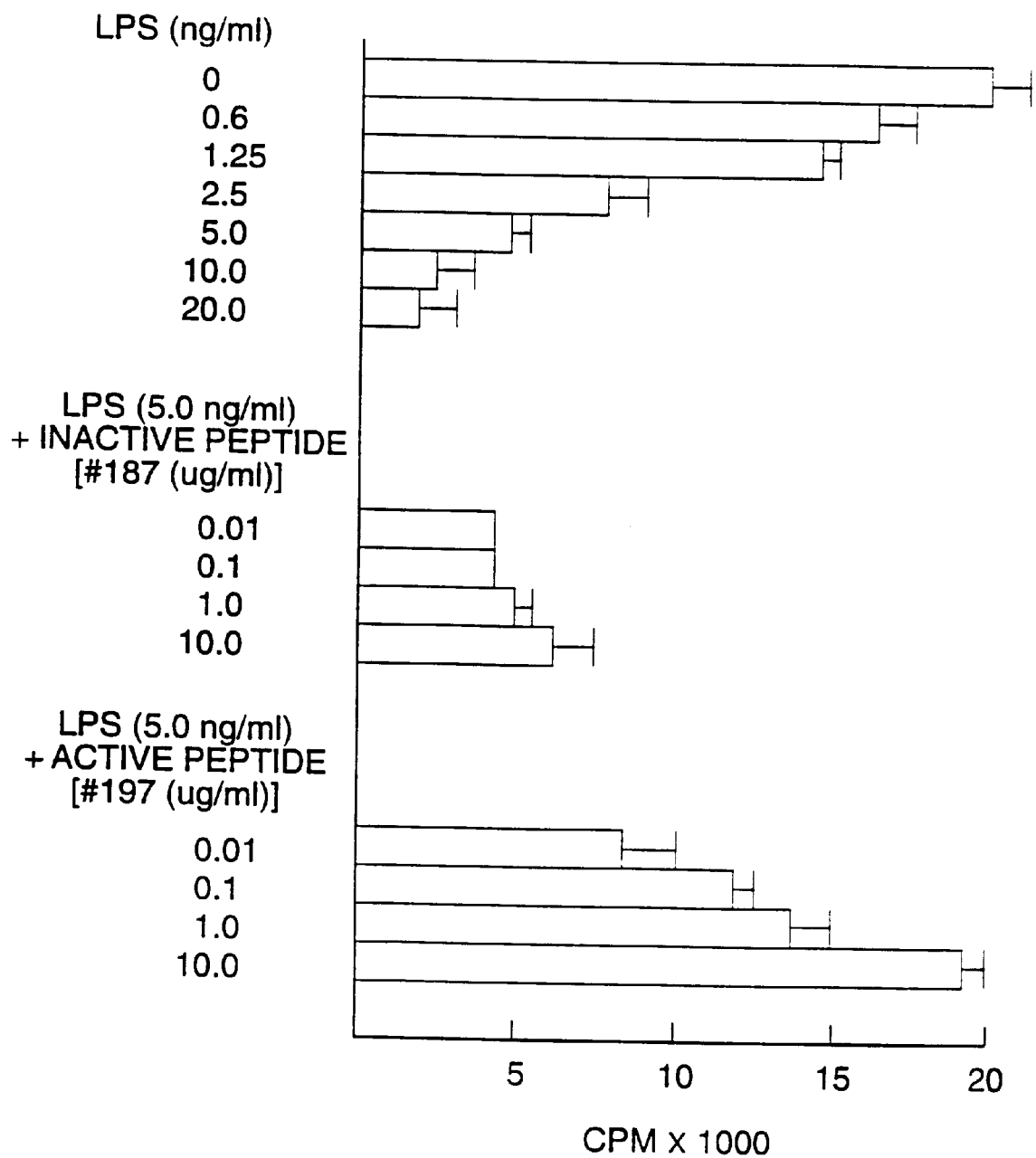
FIG. 8 is a graph illustrating the effect of RNIP on LPS-induced inhibition of RAW 264.7 cell proliferation.

When LPS is added to RAW 264.7 cells it causes a dose-dependent inhibition of proliferation with differentiation of the cells into a macrophasge phenotype. FIG. 8 shows that when RNIP is added to the cultures containing 5 ng/ml of LPS it reverses the inhibition of proliferation and activation of the RAW 264.7 macrophage cell line.

Table 6 presents a comparison of the effect of RNIP, CAP18, and defensins HP-1 and HP-2 (Territo et al. (1989) J. Clin. Invest. 84:2017–2019) on LPS-induced tissue factor generation. Tissue factor assays were performed as follows. Mouse peritoneal cells were elicted with an intraperitoneal injection of thioglycolate medium and harvested 5-days later by irrigation with pyrogen-free saline. The cells were washed with RPMI 1640 medium, counted and resuspended at a concentration of 1.5–2.0×10$^6$/ml in serum-free RPMI medium containing glutamine (0.29 mg/ml), penicillin (50 units/ml) and streptomycin (50 /ml). Adherent cells were prepared by incubating 10 ml of a cell suspension (in RPMI 1640 media in sterile culture bottle (Nunclon, 50 ml, Inter Med) for 60 min. at 37° C. in a 5% $CO_2$ atmosphere. The plastic adherent cells were recovered by scraping of the bottle with a sterile rubber policeman. The adherent cells were then washed twice with RPMI media, resuspended in serum-free medium (1×10$^6$/ml) in culture tube (Nunc cryotube, Inter Med), and stimulated with graded doses of LPS for 6 hr. at 37° C. in a 5% $CO_2$. The cell suspension was centrifuged and cell pellet was frozen at −80° C. until clotting assays were run.

Human mononuclear cells were separated from citrated peripheral blood by centrifugation over Sodium-metrizoate-Ficoll (lymphocyte Separation Medium, Japan Antibody Institute, Gumma). The resulting mixed mononuclear cell suspension was washed 3 times with RPMI 1640 media. Cell suspension (1×10$^6$/ml) was stimulated with LPS for 16 to 18 hr.

Veronal buffered saline (VBS) was added to the cell pellet, lysed by 3 cycles of freeze/thaw and sonicated for 10 sec with a hand-held sonicator microbe (Handy Sonic, model UR-20P, Tomy Seiko LTD, Tokyo). Tissue factor activity was tested in modified unactivated partial thromboplastin time (7). One tenth ml of cell lysate (1×10$^6$/ml) was preincubated with mouse plasma at 37° C. for 3 min. Then 0.1 ml of 25 mM-$CaCl_2$ which contains phospholipid was added to the mixture and clotting time was measured using a fibrometer (Bio Quest Division, Becton Dickinson, Cokeysville, USA). A standard curve obtained from serial two-fold dilutions of rabbit brain thromboplastic (Simplastin, Ono Pharmaceutical Co.) was used to transpose tissue factor activity into arbitrary tissue factor units (1 μg/ml) suspension of rabbit brain was assigned a value of 1,000 units).

Statistical analysis:

The mean tissue factor units+standard error was determined from three to four samples. Student's t test for unpair data was used to determine the statistically significant differences. A two-tailed P value of <0.05 was considered significant.

TABLE 6

RNIP and CAP18 attenuate LPS-induced tissue factor by human mononuclear cells

| Peptide | HA† Units | LPS µg/ml | Tissue Factor Units ×10³/3.6 × 10⁴ cells | Δ Units (%) | Inhibition (%) |
|---|---|---|---|---|---|
| — | — | — | 1096 ± 421 (1.0) | 0 | — |
| — | — | 0.1 | 18214 ± 4192 (16.6) | 17118 (100) | 0 |
| RNIP | 2 | 0.1 | 9438 ± 293 (9.0) | 8342 (49) | 51 |
| CAP-18 | 1 | 0.1 | 13097 ± 1946 (9.9) | 12001 (70) | 30 |
| — | — | — | 492 ± 75 (1.0) | 0 | — |
| — | — | 0.1 | 7218 ± 264 (14.7) | 6726 (100) | 0 |
| HP-1* | 4 | — | 561 ± 230 (1.1) | 69 | — |
|  | 4 | 0.1 | 8788 ± 443 (17.9) | 8296 (123) | 0 |
| HP-2* | 2 | — | 638 ± 299 (1.3) | 146 | — |
|  | 2 | 0.1 | 8443 ± 1348 (17.2) | 7951 (118) | 0 |
| RNIP | 2 | — | 636 ± 141 (1.3) | 144 | — |
|  | 2 | 0.1 | 4442 ± 982 (9.0) | 3950 (59) | 41 |
| CAP-18 | 1 | — | 583 ± 178 (1.2) | 235 | — |
|  | 1 | 0.1 | 4858 ± 1963 (9.9) | 4366 (65) | 35 |

S. minnesota Smooth-LPS (2 µg/ml) was preincubated with equal volume of each LPS-binding protein (2-8HA) at 37° C. for 45 minutes, and the mixture was added to the cells and cultured for 16 hours.
*Rabbit defensins.
†Hemagglutination units.

Table 7 shows that another cationic peptide CAP37 (Morgan et al. (1991) J. Immunol. 147:3210–3214) is unable to inhibit tissue factor generation.

TABLE 7

Effect of CAP-37 on tissue factor generation.

| LPS* µg/ml | CAP-37† HA** | Tissue factor units /1 × 10⁵ cells | Activity |
|---|---|---|---|
| — | — | 168 ± 95 (1.0) | — |
| — | 15 | 183 ± 67 (1.1) | — |
| 0.1 | — | 412 ± 30 (2.5) | 100 |
| 0.1 | 15 | 383 ± 307 (2.3) | 93.0 |
| 1.0 | — | 692 ± 27 (4.1) | 100 |
| 1.0 | 15 | 648 ± 343 (3.9) | 93.6 |

*S. minnesota Smooth-LPS.
†LPS was incubated with CAP-37 at 37° C. for 2 hours, and the mixture was added to cells, then cultured for 6 hours.
**Hemagluttination units.

This result demonstrates that another cationic protein does not inhibit LPS activity. Similar results with the defensins and histones (Table 6) suggest that RNIP is a specific inhibitor of LPS.

6. In vivo Activity of RNIP

Galactosamine sensitizes mice to the lethal effects of LPS by a factor 1000 or more. CAP18 and LPS were mixed and injected IP into sensitized mice. CAP18 can neutralize the lethal effects of LPS in this model of endotoxemia (see Table 8).

TABLE 8

CAP18 attenuates LPS toxicity in galactosamine-sensitized mice.

| Galactosamine (MG, IP) | CAP18 (µg, IP) | Re-LPS (µg, IP) | Lethality (%) groups of 10 mice |
|---|---|---|---|
| 15 | — | — | 0 |
| — | 40 | — | 0 |
| — | — | 100 | 0 |
| 15 | — | 1 | 80 |
| 15 | 4 | 1 | 10 |

7. Cloning of Human CAP18

Numerous attempts were made to identify to human CAP18 using PCR primers designed from rabbit RNIP (the C-terminal 37 amino acids of rabbit CAP18). This approach was not successful. Next duplicate filters were prepared from a million plaques and controls of a lambda gt11 human bone marrow cDNA library (Clontech Laboratories, Palo Alto, Calif.). One set of filters was screened with rabbit CAP18 cDNA and the other was screened with a rabbit RNIP probe. Both probes were labeled with $^{32}P$ using PCR. No positives were identified from a total of 500,000 plaques screened at standard stringency using the other probe. However, using the CAP18 probe, 14 putative positives were identified from a total of 500,000 plaques screened under reduced stringency. In this case temperature and salt were kept constant and formamide was reduced from 50% to 30% during prehybridization and hybridization with washing at 50° C. instead of 65° C. Six of the most intense positives were chosen for secondary screening, and four of these yielded unequivocal individual positive plaques. Lambda DNA was purified and the inserts cloned into TA sequencing vectors. One of these was a false positive, whereas three were confirmed as CAP18 cDNA's of slightly different lengths. The human CAP18 cDNA sequence is presented in SEQ ID NO:1 and the corresponding amino acid sequence is set forth in SEQ ID NO:2.

The cDNA revealed a protein with two domains: an amino terminal cystein protease inhibitor domain and a carboxy terminal endotoxin binding domain. FIG. 9 compares the cDNAs of human and rabbit CAP18. FIG. 10 compares the protein sequences of rabbit CAP 18, human CAP18 protein, and cathelin, a pig cysteine protease inhibitor. Table 9, below, compares the nucleic acid and amino acid composition homologies of the rabbit and human CAP18 proteins in both the N-terminal cysteine protease domain and the RNIP domain. There is a much higher level of amino acid conservation in the N-terminal cysteine protease inhibitor domain compared to the carboxy terminal RNIP domain.

TABLE 9

| CAP18 DOMAIN | Nucleic Acid | Amino Acid |
|---|---|---|
| Cysteine protease inhibitor | 74% | 63% |
| RNIP | 73% | 38% |

8. Bioactivity of Human RNIP

Figure 11:
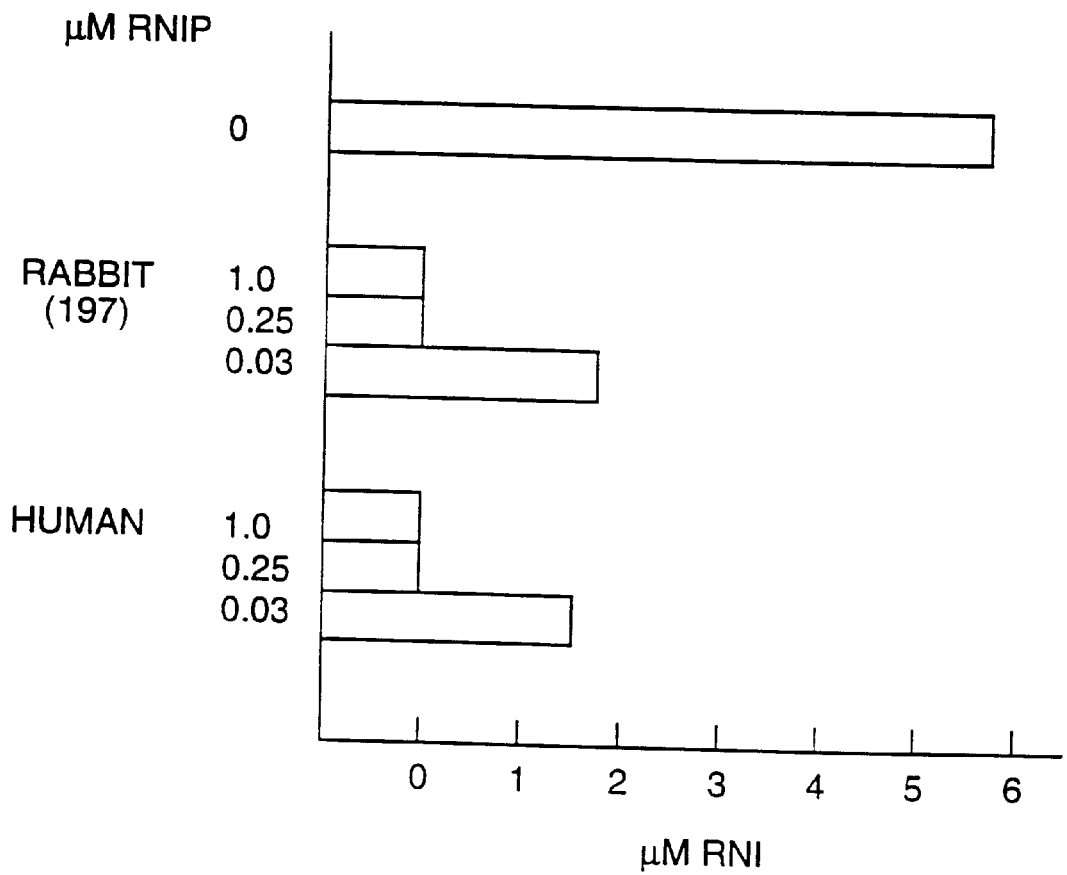
FIG. 11 is a comparison of the inhibitory effects of human RNIP and rabbit RNIP on RAW cell RNI production, as described in detail in the Experimental section hereinafter.

A human RNIP polypeptide comprising amino acids 134 to 170 of SEQ ID NO:2 was synthesized by the Merrifield solid phase synthesis method. LPS inhibition activity of human RNIP was compared with that of rabbit RNIP comprising amino acids 135 to 171 of the rabbit sequence in SEQ ID NO:4. Equimolar concentrations of both human and rabbit RNIP (1 µM, 0.25 µM, and 0.03 µM were introduced to stimulated cultures of RAW 264.7 which produce reactive nitrogen intermediates (nitric oxide) in the presence of LPS (2.5 ng/ml). The results are shown in FIG. 11.

9. Anti-Coagulant Activity of RNIP

Blood coagulation and hemostasis are important components of the host defense system against traumatic injury and invasion by microorganisms. Overwhelming infections, particularly those associated with release of endotoxin can cause excessive activation of the coagulation cascade, a condition termed disseminated intravascular coagulation (DIC). Classically the blood coagulation cascade has been divided into two parts, the intrinsic and extrinsic pathways. The intrinsic pathway is activated by conversion of factor XII to factor XIIa secondary to exposure of collagen from damaged vascular endothelial cells. The extrinsic pathway is initiated by tissue factor (procoagulant, tissue thromboplastin) expressed by activated monocytes and macrophages. Tissue factor converts factor VII to factor VIIa and the tissue factor-VIIa complex converts factor X to Xa and factor IX to factor IXa. Both pathways converge by at the generation of a prothrombinase comprised of a complex of factor Xa, factor V, phospholipid and calcium ions. Prothrombinase converts prothrombin (factor II) to thrombin (IIa). Thrombin generates fibrin monomers from fibrinogen. Because both monocytes and macrophages as well as endothelial cells are induced to synthesize tissue factor by LPS, the extrinsic pathway is thought to play an important role in LPS-induced DIC. Studies reported 25 years ago showed that granulocytes contain anti-coagulant cationic proteins (Saba et al. (1967) J. Clin. Invest. 46:580–589) that bound to heparin (Saba et al. (1968 Blood 31:369–380). Polymorphonuclear neutrophils (PMN) contain a number of cationic proteins and peptides that have been shown to have anti-microbial activities. Among the best characterized are bactericidal/permeability-increasing protein (BPI), the defensins, and azurocidin (CAP37).

We now demonstrate that the LPS binding RNIP peptides inhibit LPS induced generation of tissue factor from murine macrophages. Furthermore, we demonstrate that RNIP peptides inhibit the coagulation cascade at two sites: activation of factor X and conversion of prothrombin to thrombin (factor II to factor IIa). The putative heparin binding domain of RNIP is implicated in the inhibition of coagulation because of the high correlation of three observations: a) LPS-binding but not non-binding peptides inhibit coagulation; b) LPS-binding but not non-binding peptides contain a consensus heparin binding domain at the N-terminus of RNIP; c) peptides containing the heparin binding domain inhibit coagulation whereas those that do not contain the domain do not inhibit coagulation.

Coagulation assays were run as follows:

Clotting method: Human plasma (Ortho plasma control, Ortho Diagnostic Co.). ATPP reagent(Organo-technika, Tokyo, Japan). Standard tissue factor, rabbit brain thromboplastin (Simplastin, ONO Pharmaceutical, Tokyo, Japan). Purified human factor VII, factor X, factor Xa (Sigma Chemical Co., St. Louis, Mo.). Russell Viper venom (RVV) and Echis Carinatus venom (ECV, Sigma Co.).

Synthetic chromogenic substrate method: Substrate for factor Xa, S2222 (Kabi, Bz-Ile-Glu-Arg-pNA) was used. Substrate for factor II (prothrombin), Boc-Val-Pro-Arg-pNA (Sigma Chemical Co.) was used.

Instrumentation: Clotting assays were carried out using a Fibrometer (BioQuest Division, Becton Dickinson; Cokeysville, N.C., USA).

Tissue factor assay. Salmonella minnesota smooth LPS was incubated with each peptide (1 μg/ml) for 5 min., then the mixture was added to peritoneal murine macrophages obtained 4 days after thioglycollate stimulation. Cells were cultured for 6 hours prior to assay of tissue factor by clotting assay.

Prothrombin time (PT). Human plasma (100 μl) was incubated with 100 μl of each peptide at 37° C. for 3 min., then 100 μl of tissue factor (250 μg/ml) CaCl$_2$ was added and clotting time was measured.

Partial thromboplastin time (PTT). Human plasma (100 μl) was incubated with each peptide (100 μl) at 37° C. for 3 min., then 100 μl of CaCl$_2$ containing phospholipid was added and clotting time was measured.

Activated partial thromboplastin time (APTT). Human plasma (100 μl), 100 μl of APTT reagent and 100 μl of peptide was incubated at 37° C. for 5 min after which CaCl$_2$ was added and clotting time measured.

Factor Xa-induced clotting assay. The mixture of 100 μl human plasma, 50 μl of Xa (0.2 unit/ml) and 50 μl of each peptide (0 to 40 μg/ml) was incubated at 37° C. for 3 min., then 100 μl of 25 mM-CaCl$_2$ was added to the mixture and clotting time was measured.

Factor Xa activity using synthetic substrate. A reaction mixture of factor VII (1 unit/ml, 200 μl), factor X (1 unit/ml, 200 μl), tissue factor (2.5 mg/ml, 50 μl), 25 mM-CaCl$_2$ (50 μl) and 50 μl of several concentration of peptide was incubated at 37° C. for 10 min. To 200 Al of the reaction mixture, 60 μl of 4 mM S-2222, a synthetic substrate for factor Xa, and 340 μl of Tris-HCl buffer, pH 8.2, was added and further incubated for 15 min. The reaction was stopped by adding 60 μl of 50% acetic acid, and OD for p-nitroaniline was read at 405 nm.

Prothrombin activation by Echis Carinatus venom (ECV). A reaction mixture of prothrombin (factor II) (0.1 unit/ml, 200 μl), ECV (1 unit/ml, 200 μl), various concentration of peptide (70 μl), 50 μl of 25 mM-CaCl$_2$ and 180 μl of Tris buffer was incubated at 37° C. for 10 min. To 300 μl of the reaction mixture, 60 μl of 4 mM-thrombin substrate and 240 μl of buffer was added and further incubated for 15 min.

Prothrombin activation by factor Xa (divided into three steps).

a) Factor X activation. Factor X (1 unit/ml, 400 μl) was activated by incubating with a reaction mixture of factor VII (1 unit/ml, 400 μl), tissue factor (5 mg/ml, 100 μl) and CaCl$_2$ at 37° C. for 10 min.

b) Prothrombin (factor II) activation. To 250 μl of the reaction mixture, factor II (1 unit/ml, 50 μl), several concentration of peptide (25 μl) and phospholipid (50 μg/ml, 25 μl) was added and incubated at 37° C. for 10 min.

c) Hydrolysis of thrombin substrate. To 300 μl of the reaction mixture (step b), thrombin 60 μl of substrate and 240 μl of Tris buffer was added and further incubated for 15 min.

Interaction of heparin and synthetic peptide in a modified PT system. Each reaction mixture contained: 100 μl human plasma; 50 μl of buffer or heparin (2 units/ml); 50 μl buffer or peptide; 100 μl tissue factor (250 μg/ml).

Tissue factor lethality model. Reference tissue factor (simplastin, 1 mg/mouse) was IV injected into ddY mice (male, 20-week-old, 38–45 g) incubated with or without peptide.

10. RNIP peptides inhibit LPS-induced tissue factor generation by macrophages.

Figure 12:
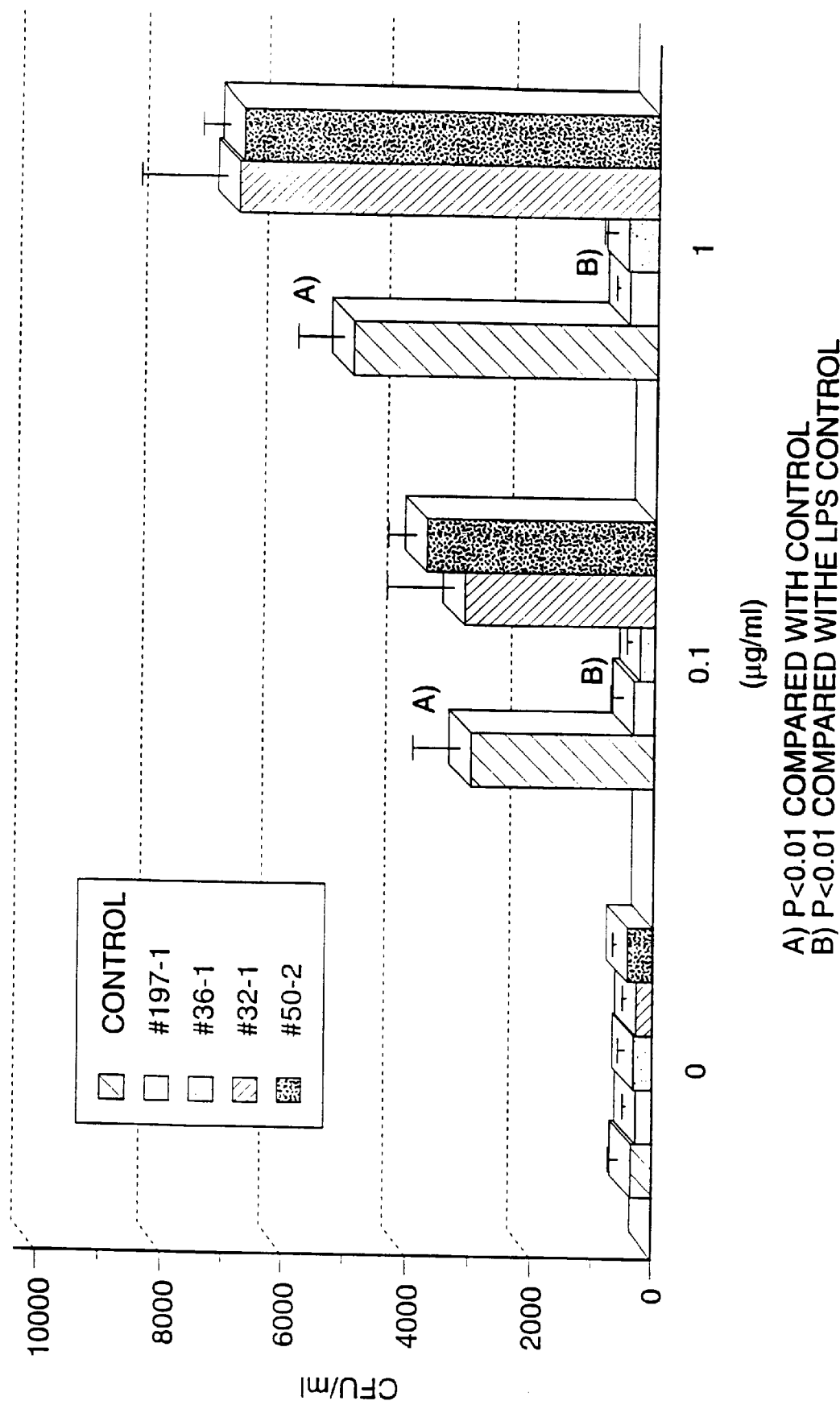
FIG. 12 is a chart comparing the effects of two active and two inactive RNIP peptides in inhibiting the LPS-induced generation of tissue factor, where Salmonella minnesota smooth LPS was incubated with peptides 197 (RNIP), 36-1, 32-1, and 50-2 (1 μg/ml) for five minutes, with the mixture then being added to thioglycolate-stimulated murine macrophages and cultured for six hours prior to assay of tissue factor by clotting assay, as described in more detail in the Experimental section hereinafter.

Various concentrations of Salmonella minnesota smooth LPS were incubated with each peptide (197 (RNIP), 36-1, 32-1, and 50-2) at 37° C. for 5 minutes prior to mixing with thioglycollate-stimulated murine peritoneal macrophages. Production of tissue factor after 6 hr. was measured by clotting assay. FIG. 12 shows tissue factor induced in response to LPS and the inhibition of this response by RNIP peptides (1 μg/ml), 197 and 36-1. The non-LPS binding peptides 32-1 and 50-2 fail to inhibit LPS induced tissue factor. In the absence of LPS no tissue factor is synthesized by these cells.

Figure 13:
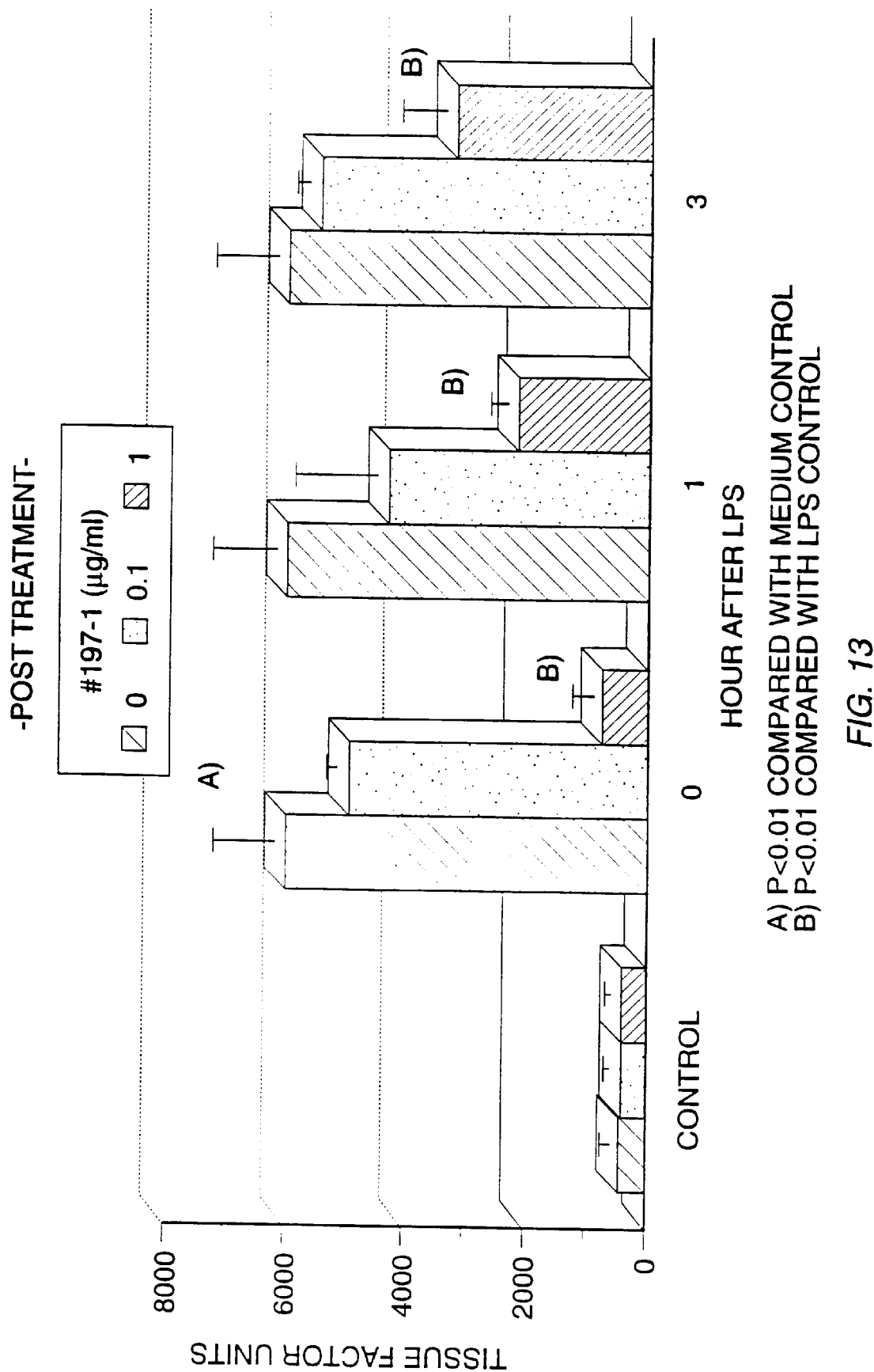
FIG. 13 compares LPS-induced tissue factor generation by RNIP (peptide 197) at different concentrations at 0, 1, and 3 hours after LPS.

Next synthetic RNIP peptide (197) was added to the LPS-stimulated macrophages at various times post-addition of the LPS stimulus. Significant inhibition of LPS-induced tissue factor generation is found even when peptide 197 is added as late as 3 hours after the LPS stimulus (FIG. 13). In summary, RNIP derived peptides having LPS binding activity inhibit LPS induction of tissue factor, whereas related cationic peptides without LPS binding activity do not inhibit LPS induction of tissue factor.

11. RNIP peptides inhibit in vitro clotting assays.

Previous studies indicated that tissue factor activity was associated with the surface membranes of granulocytes. However, homogenization or sonic disruption of these cells was observed to reduce tissue factor activity and this inhibition was ascribed to the release of cationic proteins. Because the assay for tissue factor utilizes the clotting cascade, it was reasoned that granulocyte-derived cationic proteins might directly inhibited other sites of the clotting cascade. Therefore, the RNIP peptides were tested in a series of in vitro clotting assays.

Figure 14A:
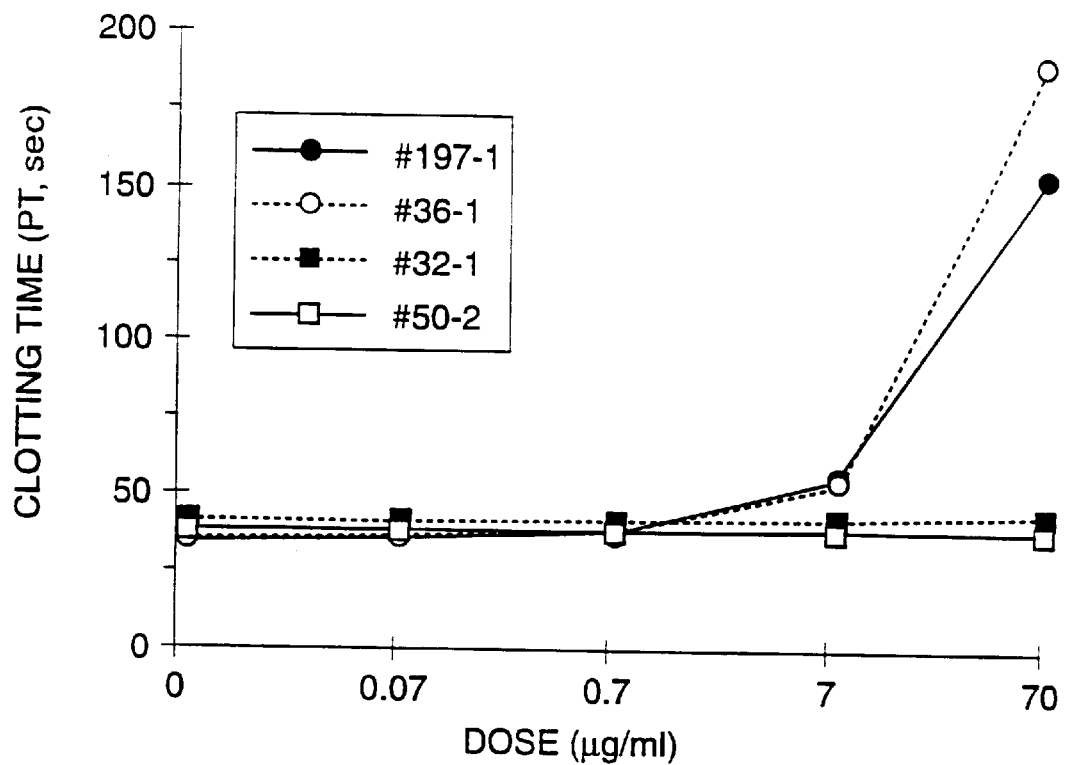
FIGS. 14A–14C illustrate anti-coagulant activity of the four peptides of FIG. 12 as a function of dosage, for prothrombin time (PT), partial thromboplastin time (PTT), and activated partial thromboplastin time (aPTT), respectively.
Figure 14B:
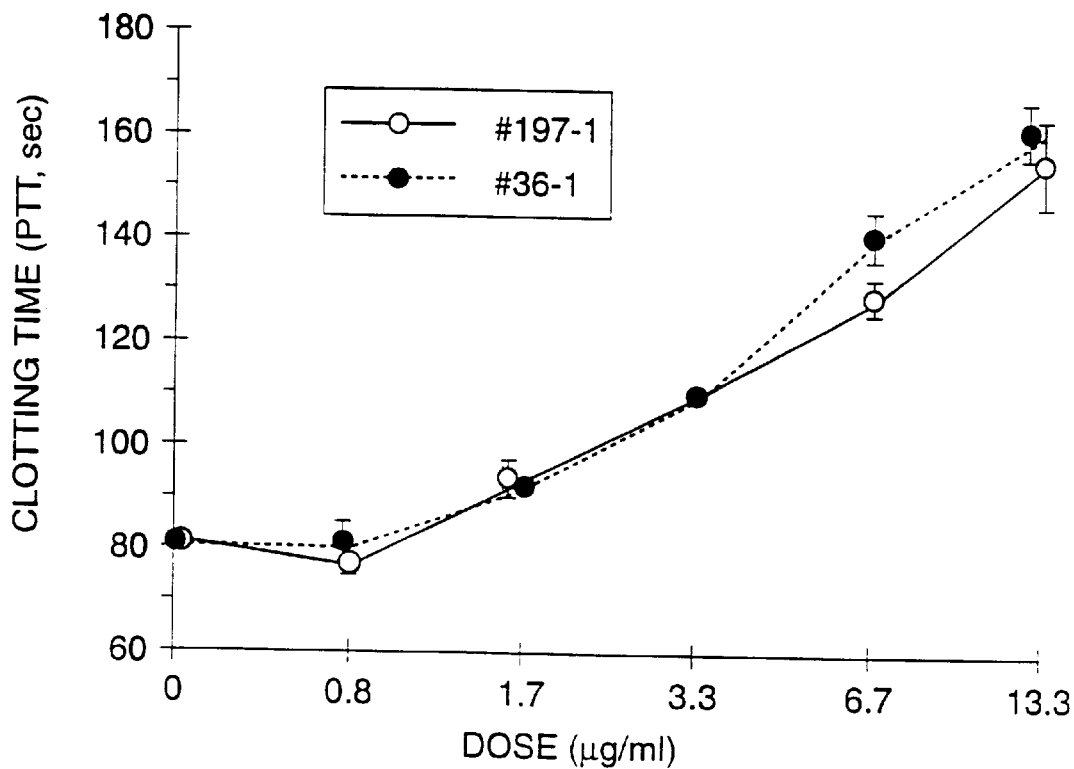
Figure 14C:
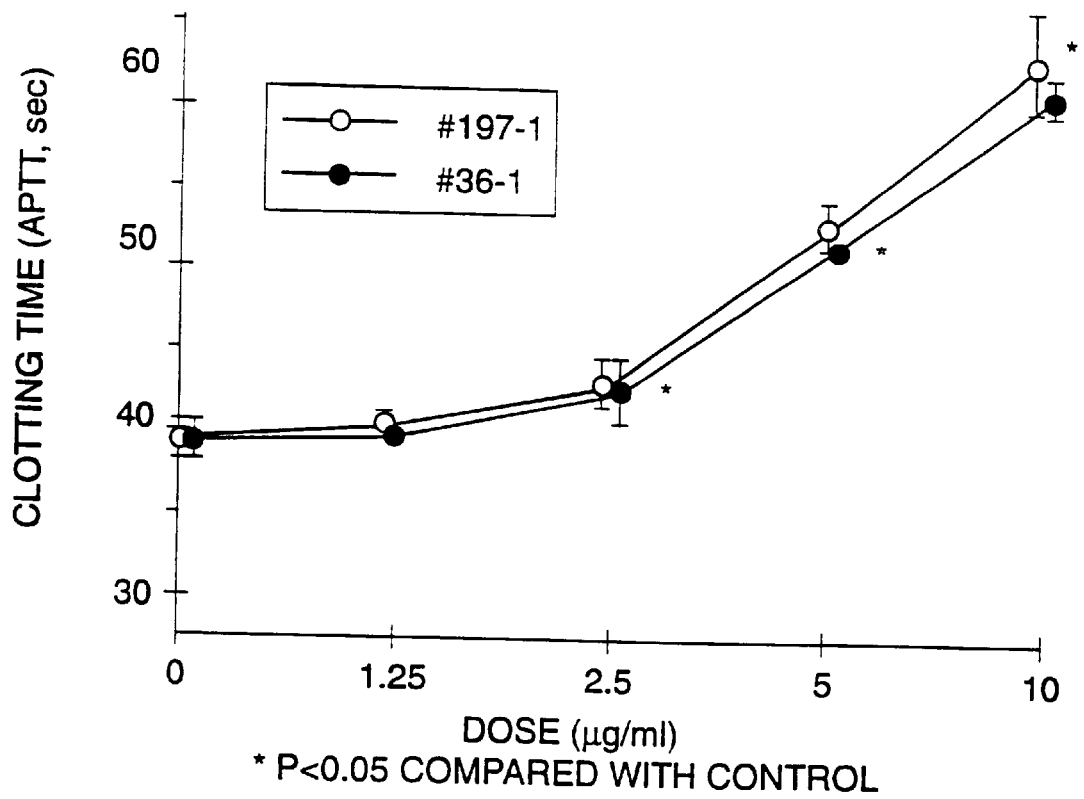

The active peptides, 197 (RNIP) and 36-1, but not the inactive peptides, 32-1 and 50-2, inhibited the prothrombin time (PT), FIG. 14A. Additional studies focused on the active peptides. Both peptides inhibited the partial thromboplastin time (PTT), FIG. 14B; and the activated partial thromboplastin time (aPTT), FIG. 14C; all in a dose dependent manner. Finally none of the peptides was able to inhibit thrombin induced clotting even at concentrations of peptide up to 10 μg/ml (data not shown).

Figure 15A:
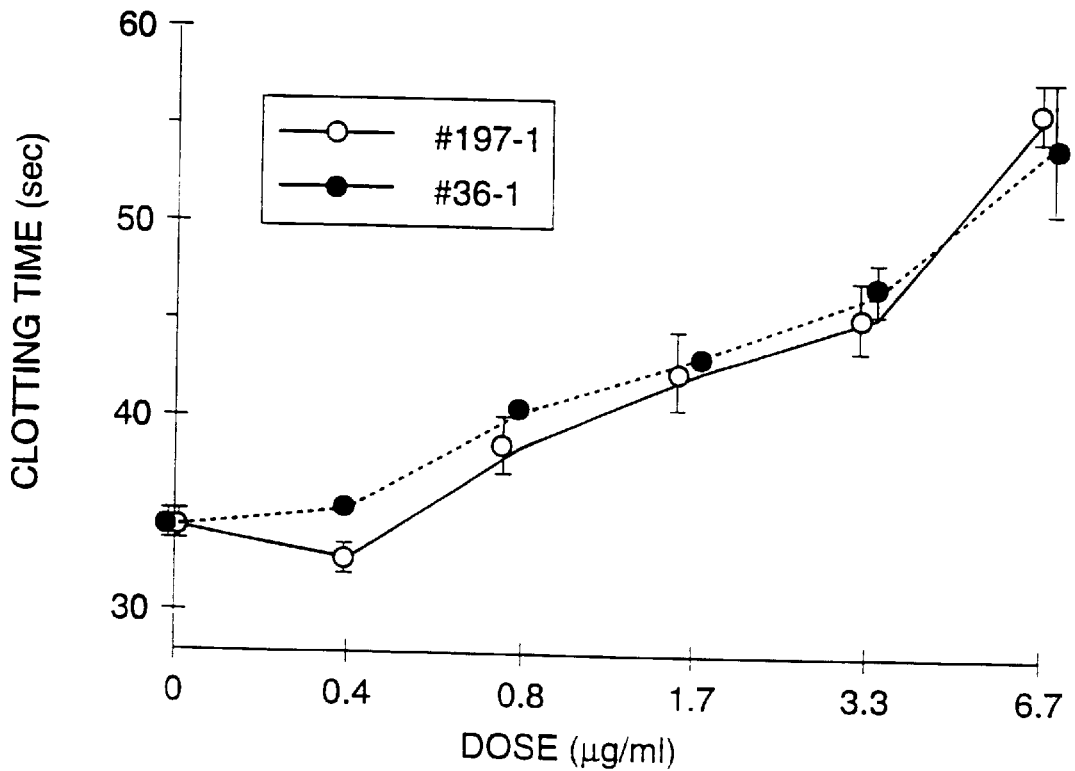
FIGS. 15A and 15B illustrate the effect of active synthetic peptides 197 and 36-1 on factor Xa-induced clotting and factor X activating enzyme, respectively.
Figure 15B:
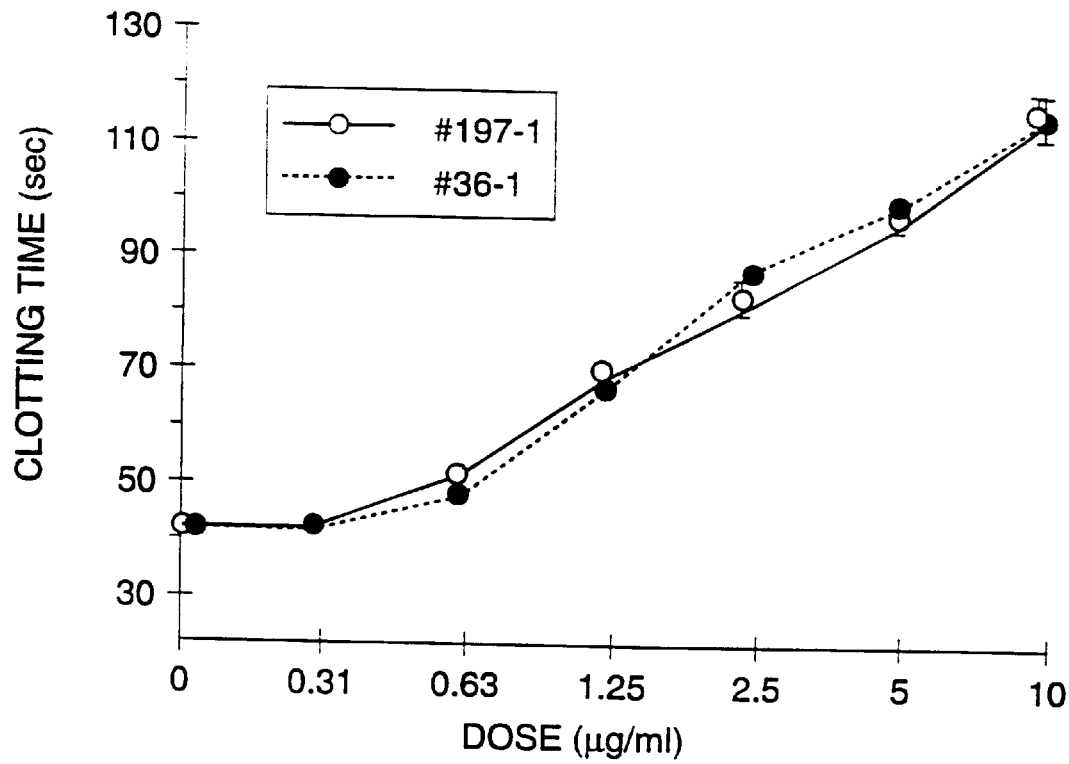

Results of these conventional in vitro clotting assays suggested that the peptides might be inhibiting a step common to both the intrinsic and extrinsic pathways. Therefore two assays were carried out to study factor X. In the first case the active peptides 197 and 36-1 were shown to inhibit Factor Xa induced clotting (FIG. 15A) and in the second case they were shown to inhibit Russell Viper Venom (RVV) activated clotting (FIG. 15B). The $IC_{50}$'s for the initial clotting studies are summarized in Table 10.

TABLE 10

In vitro anti-clotting activity of synthetic RNIP peptides

| Clotting Method | #197-1 [$IC_{50}$-μg/ml (μM)] | #36-1 [$IC_{50}$-μg/ml (μM)] |
|---|---|---|
| Activate Partial Thromboplastin time | 3.2 (0.5) | 3.8 (0.7) |
| Prothrombin time | 1.9 (0.3) | 2.0 (0.4) |
| Russell Viper Venom induced clotting | 0.7 (0.1) | 0.9 (0.2) |
| Xa-induced clotting | 2.7 (0.5) | 2.2 (0.4) |

12. Inhibition of factor X activation [X→Xa] by RNIP peptides.

Figure 16A:
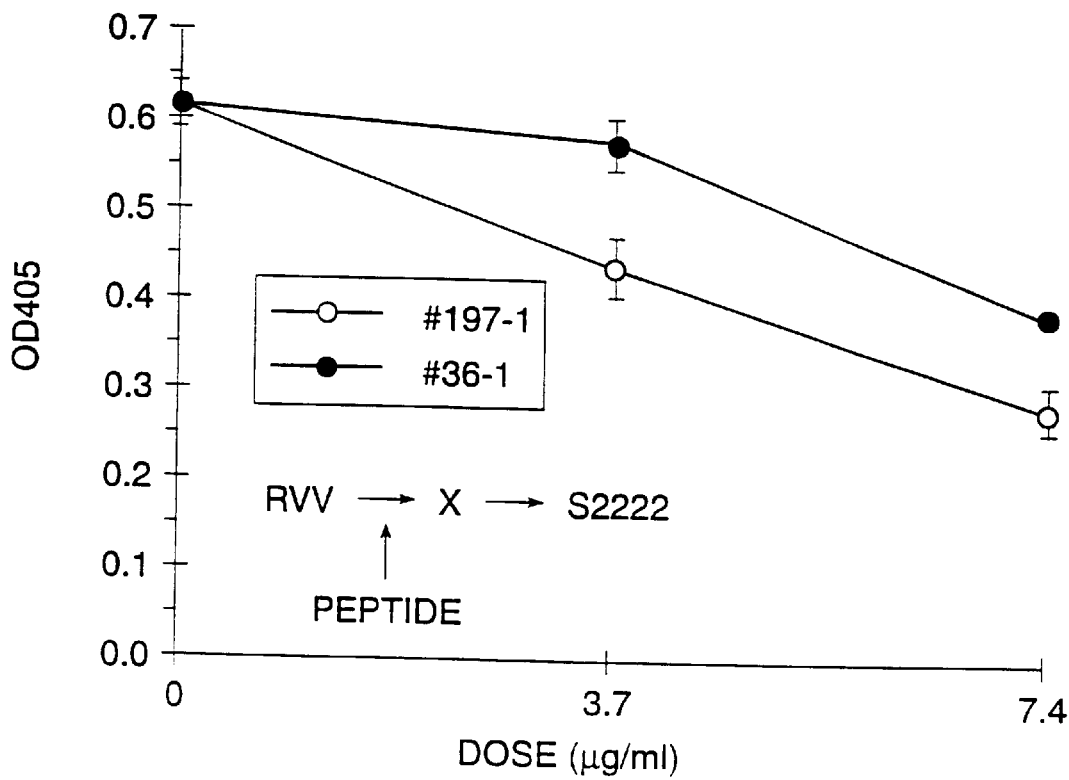
FIGS. 16A and 16B compare peptides 197 (RNIP) and 36-1 with respect to effect on factor X activating enzyme and inhibition of factor Xa generation, respectively.
Figure 16B:
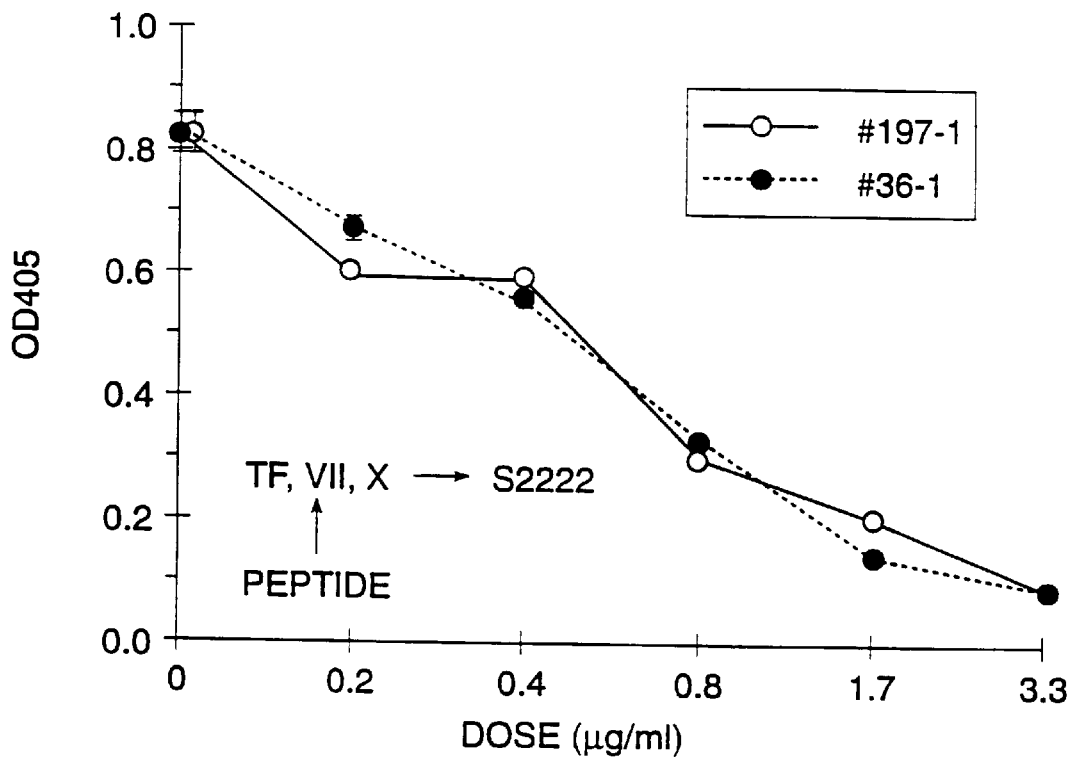

Because initial studies demonstrated peptide inhibition of factor Xa induced clotting, direct inhibition of Xa by the peptides was measured using Xa substrate S2222. No evidence of direct Xa inhibition was found using RNIP peptides 197 or 36-1 at concentrations over 10 μg/ml (Table 11). Next the effect of the RNIP peptides on the conversion of factor X to Xa was studied by two methods. In the first case peptides 197 and 36-1 inhibited direct RVV activation of factor X to Xa with $IC_{50}$'s of 6.7 μg/ml (1.1 μM) and 10.0 μg/ml (1.9 μM), respectively (FIG. 16A; Table 11). In the second case when factor X was activated by tissue factor and purified factor VII, both peptides demonstrated a dose dependent inhibition with $IC_{50}$'s of 0.3–0.7 μg/ml (40–100 nM) (FIG. 16B; Table 11). In summary these studies confirmed that the peptides inhibit the clotting cascade by inhibiting the conversion of factor X to Xa.

TABLE 11

Evaluation of in vitro activity of synthetic RNIP peptides using synthetic substrate

| Assay Method | #197 [$IC_{50}$-μg/ml (μM)] | #36-1 [$IC_{50}$-μg/ml (μM)] |
|---|---|---|
| A. Factor X | | |
| Direct Xa inhibition | 55–200 (9–33) | 45–250 (8–46) |
| Russell Viper venom<br>X------>Xa | 6.7 (1.1) | 10.0 (1.9) |
| Tissue factor<br>VII, X------>Xa | 0.3–0.6 (0.04–0.1) | 0.6–0.7 (0.1) |
| B. Prothrombin (Factor II) | | |
| Echis Carinatus<br>II------>IIa | 9.4 (1.5) | 10 (1.9) |
| Tissue factor<br>VII, X, II----->IIa | 2.8 (0.5) | <1.8 (<0.3) |

13. Inhibition of prothrombin activation (factor II→IIa) by RNIP peptides.

Figure 17A:
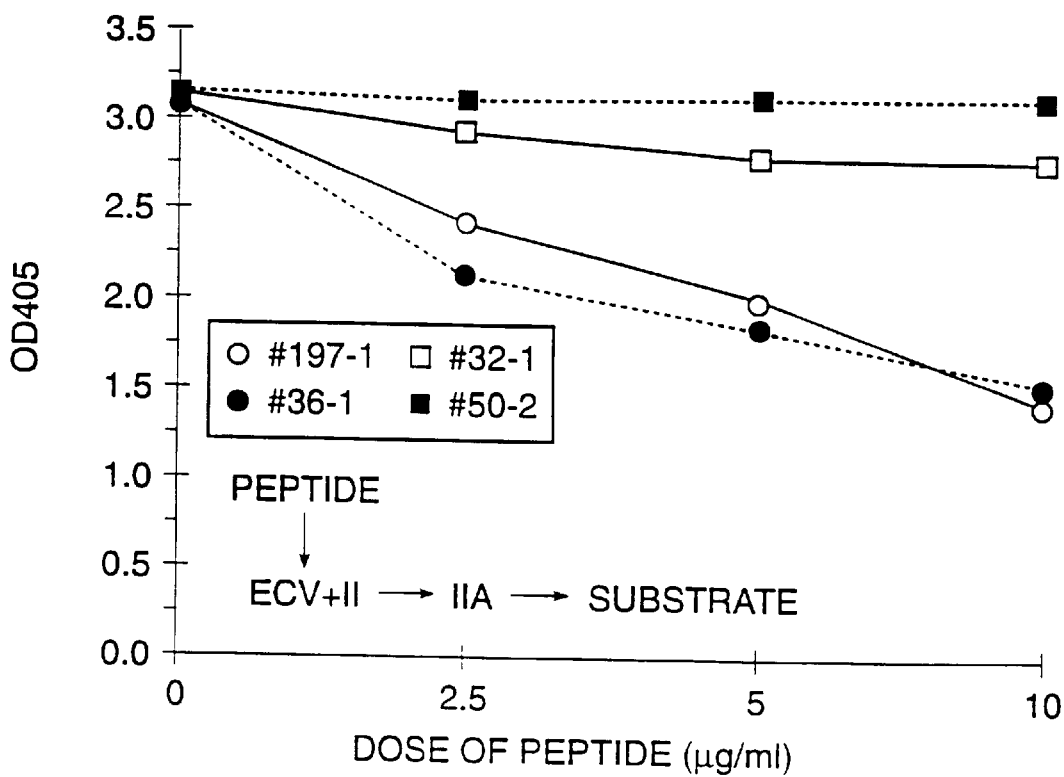
FIGS. 17A and 17B compare the effect of four test peptides on prothrombin activation by Echis carinadus venom and prothrombin activation by factor Xa, respectively.
Figure 17B:
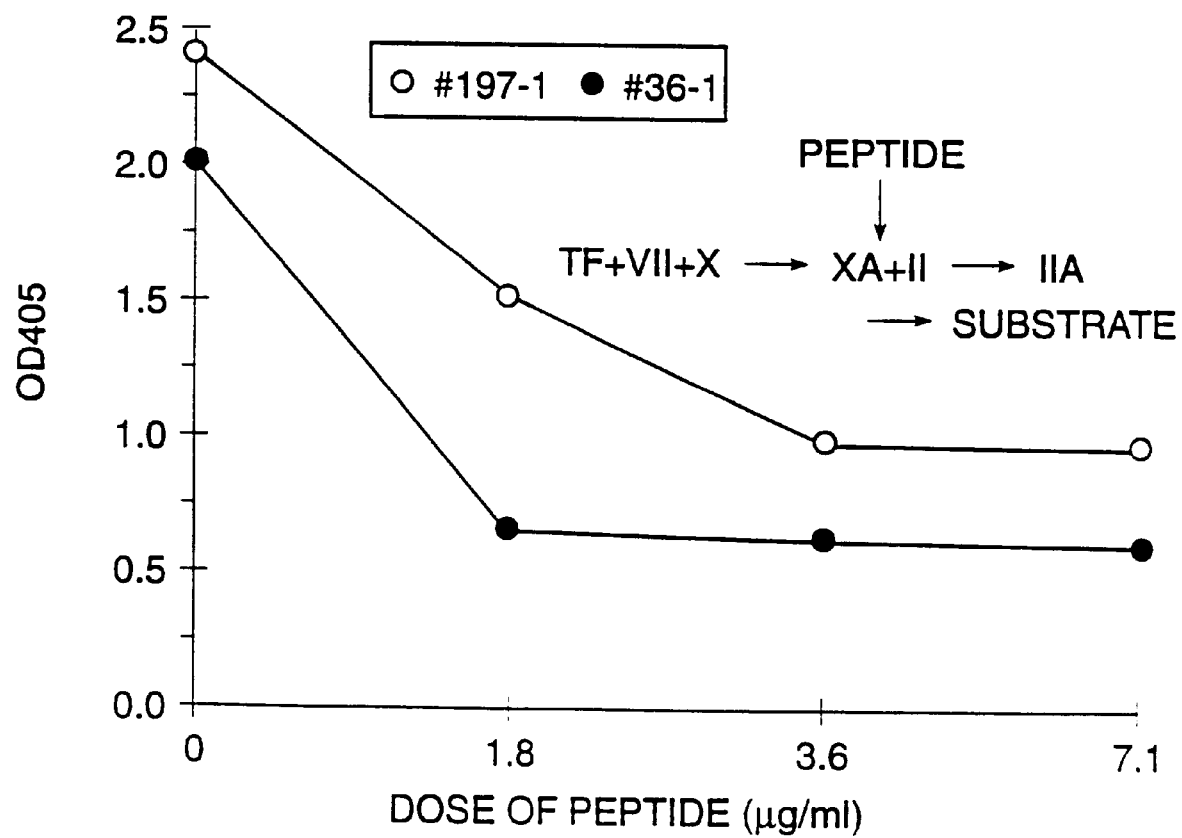

Because the peptides inhibited Xa induced clotting, we hypothesized that they acted at additional sites. No direct inhibition of thrombin was observed using a chromogenic assay (data not shown). Therefore studies of the activation of prothrombin (factor II to IIa) were carried out by two methods. In the first case active RNIP peptides 197 and 36-1 but not inactive peptides 32-1 and 50-2 inhibited *Echis carinatus* venom activation of purified factor II to IIa (see FIG. 17A;

Table 11). In the second case when factor II was activated by Xa formed by incubation of tissue factor, factor VII and factor X (as demonstrated above), both active peptides demonstrated a dose dependent inhibition. [$IC_{50}$ for 197 of 2.8 μg/ml, 50 nM; $IC_{50}$ for 36-1 of <1.8 μg/ml, <30 nM] (FIG. 17B; Table 11). In summary these studies demonstrated that the RNIP peptides inhibit the activation of prothrombin (conversion of factor II to IIa).

14. RNIP protects mice from tissue factor lethality.

The anticoagulant activity of the RNIP peptides was studied in an acute animal model. Direct injection of tissue factor IV (Simplastin, 1 mg/mouse) produces acute intravascular coagulation and death within three minutes. RNIP peptide 197 reduced mortality by 57% and prolonged survival time of tissue factor treated mice, as shown in Table 12.

TABLE 12

Synthetic RNIP peptide 197 inhibits tissue factor induced lethality in mice

| Tissue factor[a]<br>(mg/mouse) | Peptide #197<br>(μg/mouse) | No. of Mice<br>(dead/total) | Survival<br>(%) | Survival time<br>(sec) |
|---|---|---|---|---|
| — | —[b] | 0/6 | 100 | — |
| 1.0 | — | 7/7 | 0 | 187 ± 70 |

TABLE 12-continued

Synthetic RNIP peptide 197 inhibits tissue factor induced lethality in mice

| Tissue factor[a] (mg/mouse) | Peptide #197 (μg/mouse) | No. of Mice (dead/ total) | Survival (%) | Survival time (sec) |
|---|---|---|---|---|
| 1.0 | 10 | 3/7 | 57[c] | 305 ± 175 |
| 1.0 | 5 | 4/7 | 43 | 228 ± 48 |

[a]Tissue factor (Simplastin, 10 mg/ml was mixed with equal volume of synthetic peptide 100 μg/ml or 50 μg/ml and 0.2 ml of the mixture injected IV. ddY mice (20 weeks, 38–45 gm).
[b]$CaCl_2$ control (0.16 mg /0.2 ml/mouse).
[c]p < 0.05 compared with tissue factor control.

15. Discussion.

The results demonstrate the potent anti-coagulant activity of peptides derived from rabbit granulocyte protein CAP18. The cloning of rabbit CAP18 revealed that this molecule is comprised of two domains. The N-terminal domain is highly homologous to porcine cathelin originally purified as a cysteine protease inhibitor. Purified human CAP18 also demonstrates significant cysteine protease activity. The C-terminal 31 amino acid domain (RNIP) of CAP18 was identified as the LPS-binding domain when HPLC fractions were tested for their capacity to inhibit LPS-induced nitrogen radical production. A large series of RNIP derived peptides was studied for LPS binding and neutralization of LPS-induced nitric oxide release from murine macrophages. These results demonstrated that the C-terminus but not the N-terminus of the RNIP protein could be truncated with out loss of activity.

Rabbit RNIP peptides demonstrated inhibition activity in a series of standard in vitro clotting assays, including the prothrombin time, the partial thromboplastin time and the activated partial thromboplastin time, with no evidence for a direct action on thrombin. No evidence was found for a direct effect on the activity of factor Xa. Both factor Xa induced clotting (FIG. 15A) and Russell Viper Venom (RVV) activated clotting, however, were inhibited by the rabbit RNIP peptides. These results were confirmed using chromogenic assays. Thus, one activity of the active rabbit RNIP peptides is to inhibit the activation of factor Xa.

Because the peptides inhibited factor Xa induced clotting, we investigated whether they acted at additional sites possibly at the activation of prothrombin (factor II to IIa). Rabbit RNIP peptides inhibited both *Echis carinatus* venom activation of purified factor II to IIa and factor II activation by Xa formed by incubation of tissue factor, factor VII and factor X. Thus these studies identify at least two sites of inhibition of the clotting cascade: activation of factor X and activation of prothrombin. The precise mechanism of inhibition is not clear. Since both of these coagulation steps require phospholipids, however, it is possible that the peptides interfere with the activity of these enzymes by binding to phospholipids required for activity. Several molecules with this type of activity have been described previously. For example, Maki et al. (1984) Europ. J. Obsted. Gynec. Reprod. Biol. 17:149–154, isolated an anticoagulant protein from human placenta that bound to calcium and phospholipids. This protein belongs to the annexin family of proteins (greisow). However, the observation that activation of factor X by Russell viper venom and prothrombin by *Echis carinatus* venom does not require phospholipid, suggests that the inhibition of these steps in the clotting cascade by the peptides may be more complex than simple phospholipid binding.

We infer that rabbit CAP18 has a high affinity binding site for heparin because it was eluted from heparin-sepharose at high NaCl concentration (2.0M). Consistent with this inference is the finding of a high content of basic amino acids particularly in the C-terminal RNIP domain. Table 13 presents a sequence comparison of RNIP with a series of known heparin binding proteins. Many of these proteins contain a consensus peptide sequence, X-B-B-X-X-B-B-B-X-X-B-B-X-X (SEQ ID NO:9), where B is a basic amino acid and X is any amino acid (Sobel et al, (1992) J. Biol. Chem. 267:8857–8862). This sequence appears at the N-terminus of RNIP. We hypothesize that this domain of RNIP is not only important for heparin binding but that it participates in LPS binding. Comparison of the sequences of the active and inactive fragments of RNIP reveals that inactive fragments lack this intact heparin binding domain. Human RNIP peptide lacks the consensus heparin binding domain present in the highly active rabbit RNIP. Although human RNIP maintains some of the anti-LPS activities of rabbit RNIP, preliminary studies indicate that human RNIP lacks significant anti-coagulant activity. These findings corroborate the heparin-binding hypothesis.

TABLE 13

| | | |
|---|---|---|
| Consensus peptide | A K R G L R H R L G R K G Y | (SEQ ID NO:10) |
| | X B B X X B B X X B B X X | (SEQ ID NO:9) |
| RNIP |     G L R K R L R K F R N K I K E K | (SEQ ID NO:11) |
| | X X B B B X B B X B X B X B | (SEQ ID NO:12) |
| Lipoprotein lipase | K S S R K A R V K N I E | (SEQ ID NO:13) |
| | B X X B B X B X B X X X | (SEQ ID NO:14) |
| Apo B | K L G R K R T L R T T G | (SEQ ID NO:15) |
| | B X X B B B X X B X X X | (SEQ ID NO:16) |
| Apo E | R L L R K R L K R L H S | (SEQ ID NO:17) |
| | B X X B B B X B B X B X | (SEQ ID NO:18) |
| Thrombin | Y T H V F R L K K W I Q K | (SEQ ID NO:19) |
| | X X B X X B X B B X X X B | (SEQ ID NO:20) |
| Vitronectin | A K K Q R F R H R N R K G Y R S | (SEQ ID NO:21) |
| | X B B X B X B B B X B B X X B X | (SEQ ID NO:22) |

TABLE 13-continued

| | | |
|---|---|---|
| ECGF/aFGF | T Y I S K K H A E K H W F | (SEQ ID NO:23) |
| | X X X X B B B X X B B X X | (SEQ ID NO:24) |
| Fibrontectin | A T P I R H R P R P Y | (SEQ ID NO:25) |
| | X X X X B B B X B X X | (SEQ ID NO:26) |
| Human TFPI | K T K R K R K K Q R V K | (SEQ ID NO:27) |
| | B X B B B B B B X B X B | (SEQ ID NO:28) |
| Rabbit TFPI | K T K R K K K K Q R P V | (SEQ ID NO:29) |
| | B X B B B B B B X B X X | (SEQ ID NO:30) |

B: positive charged residue
X: any other residue
ECGF: Endothelial cell growth factor
aFGF: Acidic fibroblast growth factor
TFPI: Tissue factor pathway inhibitor A correlation of anti-coagulant activity with the intact heparin binding domain was found. Heparin and heparinoids have been intensely studied in recent years as anti-coagulants. Heparin is thought to mediate its activity by binding to antithrombin III to increase its affinity for thrombin. The activity of protease inhibitor tissue factor pathway inhibitor (TFPI) an inhibitor of factor VIIa and factor Xa is also enhanced by heparin. RNIP may interact with anionic domains on target proteins, cell surface heparans or other negatively charged carbohydrates because of its high basic charge. Although the target molecules are unknown, limited structural studies indicate a high degree of specificity in the the activity of RNIP, a finding shared with the oppositely charged heparinoids.

Although the foregoing invention has been described in some detail by way of illustration and example, for purposes of clarity of understanding, it will be obvious that certain changes and modifications may be practiced within the scope of the appended claims.

What is claimed is:

1. Human\cDNA as set forth in SEQ ID NO: 1 or complementary to said sequence.

* * * * *

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 584 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGAAGACCC AAAGGGATGG CCACTCCCTG GGGCGGTGGT CACTGGTGCT CCTGCTGCTG      60

GGCCTGGTGA TGCCTCTGGC CATCATTGCC CAGGTCCTCA GCTACAAGGA AGCTGTGCTT     120

CGTGCTATAG ATGGCATCAA CCAGCGGTCC TCGGATGCTA ACCTCTACCG CCTCCTGGAC     180

CTGGACCCCA GGCCCACGAT GGATGGGGAC CCAGACACGC CAAAGCCTGT GAGCTTCACA     240

GTGAAGGAGA CAGTGTGCCC CAGGACGACA CAGCAGTCAC CAGAGGATTG TGACTTCAAG     300

AAGGACGGGC TGGTGAAGCG GTGTATGGGG ACAGTGACCC TCAACCAGGC CAGGGGCTCC     360

TTTGACATCA GTTGTGATAA GGATAACAAG AGATTTGCCC TGCTGGGTGA TTTCTTCCGG     420

AAATCTAAAG AGAAGATTGG CAAAGAGTTT AAAAGAATTG TCCAGAGAAT CAAGGATTTT     480

TTGCGGAATC TTGTACCCAG GACAGAGTCC TAGTGTGTGC CCTACCCTGG CTCAGGCTTC     540

TGGGCTCTGA GAAATAAACT ATGAGAGCAA TTTCAAAAAA AAAA                      584
```

(2) INFORMATION FOR SEQ ID NO:2:

(i) SEQUENCE CHARACTERISTICS:
     (A) LENGTH: 170 amino acids
     (B) TYPE: amino acid
     (C) STRANDEDNESS: single
     (D) TOPOLOGY: linear (ii) MOLECULE TYPE: protein (xi) SEQUENCE DESCRIPTION: SEQ ID NO:2:

Met Lys Thr Gln Arg Asp Gly His Ser Leu Gly Arg Trp Ser Leu Val
1               5                   10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
            35                  40                  45

Arg Ser Ser Asp Ala Asn Leu Tyr Arg Leu Leu Asp Leu Asp Pro Arg
50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
                100                 105                 110

Thr Leu Asn Gln Ala Arg Gly Ser Phe Asp Ile Ser Cys Asp Lys Asp
            115                 120                 125

Asn Lys Arg Phe Ala Leu Leu Gly Asp Phe Phe Arg Lys Ser Lys Glu
130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

(2) INFORMATION FOR SEQ ID NO:3:

(i) SEQUENCE CHARACTERISTICS:
         (A) LENGTH: 587 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:3:

```
ATGGAGACCC ATAAGCACGG ACCTTCCCTG GCCTGGTGGT CACTGTTGCT GCTGCTGCTG      60

GGCCTGCTGA TGCCCCCAGC CATCGCCCAG GACCTCACCT ACCGGGAGGC TGTGCTCCGC     120

GCTGTGGATG CCTTCAACCA GCAGTCCTCA GAGGCCAACC TCTACCGCCT CCTGAGCATG     180

GACCCCCAGC AGCTGGAGGA TGCGAAGCCA TACACCCCGC AGCCTGTGAG CTTTACGGTG     240

AAGGAGACGG AGTGCCCCCG GACAACATGG AAGCTACCAG AGCAGTGTGA CTTCAAGGAA     300

GATGGGCTGG TGAAGCGGTG TGTGGGGACT GTGACACGGT ACCAGGCCTG GGACTCCTTT     360

GACATCCGCT GCAACAGGGC CCAAGAGTCC CCAGAACCTA CTGGGCTGCG CAAGCGCTTA     420

CGAAAATTTA GAAACAAGAT TAAAGAAAAG CTTAAAAAAA TTGGTCAGAA AATCCAGGGT     480

TTGCTGCCGA AACTTGCACC CAGGACAGAT TACTAGGGTC TGCCCTGCCC TGGACTCTGA     540

AAAATAAACT GTGTGAAAGC AACAAAAAAA AAAAAAAAA AAAAAA                    587
```

(2) INFORMATION FOR SEQ ID NO:4:

(i) SEQUENCE CHARACTERISTICS:
    (A) LENGTH: 171 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:4:

Met Glu Thr His Lys His Gly Pro Ser Leu Ala Trp Trp Ser Leu Leu
1               5                   10                  15

Leu Leu Leu Leu Gly Leu Leu Met Pro Pro Ala Ile Ala Gln Asp Leu
            20                  25                  30

Thr Tyr Arg Glu Ala Val Leu Arg Ala Val Asp Ala Phe Asn Gln Gln
        35                  40                  45

Ser Ser Glu Ala Asn Leu Tyr Arg Leu Leu Ser Met Asp Pro Gln Gln
    50                  55                  60

Leu Glu Asp Ala Lys Pro Tyr Thr Pro Gln Pro Val Ser Phe Thr Val
65                  70                  75                  80

Lys Glu Thr Glu Cys Pro Arg Thr Thr Trp Lys Leu Pro Glu Gln Cys
                85                  90                  95

Asp Phe Lys Glu Asp Gly Leu Val Lys Arg Cys Val Gly Thr Val Thr
                100                 105                 110

Arg Tyr Gln Ala Trp Asp Ser Phe Asp Ile Arg Cys Asn Arg Ala Gln
        115                 120                 125

Glu Ser Pro Glu Pro Thr Gly Leu Arg Lys Arg Leu Arg Lys Phe Arg
    130                 135                 140

Asn Lys Ile Lys Glu Lys Leu Lys Ile Gly Gln Lys Ile Gln Gly
145                 150                 155                 160

Leu Leu Pro Lys Leu Ala Pro Arg Thr Asp Tyr
                165                 170

(2) INFORMATION FOR SEQ ID NO:5:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Gln Leu Arg Tyr Arg Glu Ala Val Leu Arg Ala Val Asp Arg Leu Asn
1               5                   10                  15

Glu Gln Ser Ser Glu Ala Asn Leu Tyr Arg Leu Leu Glu Leu Asp Gln
            20                  25                  30

Pro Pro Lys Ala Asp Glu Asp Pro Gly Thr Pro Lys Pro Val Ser Phe
        35                  40                  45

Thr Val Lys Glu Thr Val Cys Pro Arg Thr Thr Arg Gln Pro Pro Glu
    50                  55                  60

Leu Cys Asp Phe Lys Glu Lys Gln Cys Val Gly Thr Val Thr Leu Asn
65                  70                  75                  80

Pro Ser Ile His Ser Leu Asp Ile Ser Cys Asn Glu Ile Gln Ser Val
                85                  90                  95

(2) INFORMATION FOR SEQ ID NO:6:

(i) SEQUENCE CHARACTERISTICS:

(A) LENGTH: 37 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Leu Leu Arg Lys Arg Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

(2) INFORMATION FOR SEQ ID NO:7:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Region
            (B) LOCATION: 23
            (D) OTHER INFORMATION: /note= "Xaa is Asp or Lys"

(ix) FEATURE:
            (A) NAME/KEY: Region
            (B) LOCATION: 26
            (D) OTHER INFORMATION: /note= "Xaa is a Gln or Ile"

(ix) FEATURE:
            (A) NAME/KEY: Region
            (B) LOCATION: 27
            (D) OTHER INFORMATION: /note= "Xaa is a Gly or Gln"

(xi) SEQUENCE DESCRIPTION: SEQ ID NO:7:

Gly Leu Arg Lys Arg Leu Arg Lys Phe Arg Asn Lys Ile Lys Glu Lys
1               5                   10                  15

Leu Lys Lys Ile Gly Gln Xaa Ile Gln Xaa Xaa Leu Leu
                20                  25

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:8:

AAYAARATHA ARGARAARCT                                                    20

(2) INFORMATION FOR SEQ ID NO:9:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Region
            (B) LOCATION: 2

(D) OTHER INFORMATION: /note= "Xaa is a basic amino acid."

(ix) FEATURE:
          (A) NAME/KEY: Region
          (B) LOCATION: 3
          (D) OTHER INFORMATION: /note= "Xaa is a basic amino acid."

(ix) FEATURE:
          (A) NAME/KEY: Region
          (B) LOCATION: 6..8
          (D) OTHER INFORMATION: /note= "Xaa is a basic amino acid."

(ix) FEATURE:
          (A) NAME/KEY: Region
          (B) LOCATION: 11..12
          (D) OTHER INFORMATION: /note= "Xaa is a basic amino acid."

(xi) SEQUENCE DESCRIPTION: SEQ ID NO:9:

Xaa Xaa Xaa Xaa Xaa Xaa Xaa Xaa Xaa Xaa Xaa Xaa Xaa Xaa
1               5                   10

(2) INFORMATION FOR SEQ ID NO:10:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:10:

Ala Lys Arg Gly Leu Arg His Arg Leu Gly Arg Lys Gly Tyr
1               5                   10

(2) INFORMATION FOR SEQ ID NO:11:

(i) SEQUENCE CHARACTERISTICS:
          (A) LENGTH: 16 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:11:

Gly Leu Arg Lys Arg Leu Arg Lys Phe Arg Asn Lys Ile Lys Glu Lys
1               5                   10                  15

(2) INFORMATION FOR SEQ ID NO:12:

(i) SEQUENCE CHARACTERISTICS:
          (A) LENGTH: 16 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Region
          (B) LOCATION: 3..5
          (D) OTHER INFORMATION: /note= "Xaa is a basic amino acid."

(ix) FEATURE:
          (A) NAME/KEY: Region
          (B) LOCATION: 7..8
          (D) OTHER INFORMATION: /note= "Xaa is a basic amino acid."

(ix) FEATURE:
          (A) NAME/KEY: Region
          (B) LOCATION: 10
          (D) OTHER INFORMATION: /note= "Xaa is a basic amino acid."

```
        (ix) FEATURE:
             (A) NAME/KEY: Region
             (B) LOCATION: 12
             (D) OTHER INFORMATION: /note= "Xaa is a basic amino acid."

(ix) FEATURE:
             (A) NAME/KEY: Region
             (B) LOCATION: 14
             (D) OTHER INFORMATION: /note= "Xaa is a basic amino acid."

(ix) FEATURE:
             (A) NAME/KEY: Region
             (B) LOCATION: 16
             (D) OTHER INFORMATION: /note= "Xaa is a basic amino acid."

(xi) SEQUENCE DESCRIPTION: SEQ ID NO:12:

Xaa Xaa Xaa Xaa Xaa Xaa Xaa Xaa Xaa Xaa Xaa Xaa Xaa Xaa Xaa Xaa
1               5                  10                  15

(2) INFORMATION FOR SEQ ID NO:13:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Lys Ser Ser Arg Lys Ala Arg Val Lys Asn Ile Glu
1               5                  10

(2) INFORMATION FOR SEQ ID NO:14:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (ix) FEATURE:
             (A) NAME/KEY: Region
             (B) LOCATION: 1
             (D) OTHER INFORMATION: /note= "Xaa is a basic amino acid."

(ix) FEATURE:
             (A) NAME/KEY: Region
             (B) LOCATION: 4
             (D) OTHER INFORMATION: /note= "Xaa is a basic amino acid."

(ix) FEATURE:
             (A) NAME/KEY: Region
             (B) LOCATION: 5
             (D) OTHER INFORMATION: /note= "Xaa is a basic amino acid."

(ix) FEATURE:
             (A) NAME/KEY: Region
             (B) LOCATION: 7
             (D) OTHER INFORMATION: /note= "Xaa is a basic amino acid."

(ix) FEATURE:
             (A) NAME/KEY: Region
             (B) LOCATION: 9
             (D) OTHER INFORMATION: /note= "Xaa is a basic amino acid."

(xi) SEQUENCE DESCRIPTION: SEQ ID NO:14:

Xaa Xaa Xaa Xaa Xaa Xaa Xaa Xaa Xaa Xaa Xaa Xaa
1               5                  10
```

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Lys Leu Gly Arg Lys Arg Thr Leu Arg Thr Thr Gly
1               5                   10

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 1
        (D) OTHER INFORMATION: /note= "Xaa is a basic amino acid."

(ix) FEATURE:
        (A) NAME/KEY: Region
        (B) LOCATION: 4
        (D) OTHER INFORMATION: /note= "Xaa is a basic amino acid."

(ix) FEATURE:
        (A) NAME/KEY: Region
        (B) LOCATION: 5
        (D) OTHER INFORMATION: /note= "Xaa is a basic amino acid."

(ix) FEATURE:
        (A) NAME/KEY: Region
        (B) LOCATION: 6
        (D) OTHER INFORMATION: /note= "Xaa is a basic amino acid."

(ix) FEATURE:
        (A) NAME/KEY: Region
        (B) LOCATION: 9
        (D) OTHER INFORMATION: /note= "Xaa is a basic amino acid."

(xi) SEQUENCE DESCRIPTION: SEQ ID NO:16:

Xaa Xaa Xaa Xaa Xaa Xaa Xaa Xaa Xaa Xaa Xaa Xaa
1               5                   10

(2) INFORMATION FOR SEQ ID NO:17:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Arg Leu Leu Arg Lys Arg Leu Lys Arg Leu His Ser
1               5                   10

(2) INFORMATION FOR SEQ ID NO:18:

(i) SEQUENCE CHARACTERISTICS:
        (A) LENGTH: 12 amino acids
        (B) TYPE: amino acid
        (C) STRANDEDNESS: single (D) TOPOLOGY: linear (ii) MOLECULE TYPE: peptide (ix) FEATURE:
          (A) NAME/KEY: Region
          (B) LOCATION: 1
          (D) OTHER INFORMATION: /note= "Xaa is a basic amino acid."

(ix) FEATURE:
          (A) NAME/KEY: Region
          (B) LOCATION: 4..6
          (D) OTHER INFORMATION: /note= "Xaa is a basic amino acid."

(ix) FEATURE:
          (A) NAME/KEY: Region
          (B) LOCATION: 8
          (D) OTHER INFORMATION: /note= "Xaa is a basic amino acid."

(ix) FEATURE:
          (A) NAME/KEY: Region
          (B) LOCATION: 9
          (D) OTHER INFORMATION: /note= "Xaa is a basic amino acid."

(ix) FEATURE:
          (A) NAME/KEY: Region
          (B) LOCATION: 11
          (D) OTHER INFORMATION: /note= "Xaa is a basic amino acid."

(xi) SEQUENCE DESCRIPTION: SEQ ID NO:18:

Xaa Xaa Xaa Xaa Xaa Xaa Xaa Xaa Xaa Xaa Xaa Xaa
1               5                   10

(2) INFORMATION FOR SEQ ID NO:19:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:19:

Tyr Thr His Val Phe Arg Leu Lys Lys Trp Ile Gln Lys
1               5                   10

(2) INFORMATION FOR SEQ ID NO:20:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Region
          (B) LOCATION: 3
          (D) OTHER INFORMATION: /note= "Xaa is a basic amino acid."

(ix) FEATURE:
          (A) NAME/KEY: Region
          (B) LOCATION: 6
          (D) OTHER INFORMATION: /note= "Xaa is a basic amino acid."

(ix) FEATURE:
          (A) NAME/KEY: Region
          (B) LOCATION: 8
          (D) OTHER INFORMATION: /note= "Xaa is a basic amino acid."

(ix) FEATURE:
          (A) NAME/KEY: Region
          (B) LOCATION: 9

(D) OTHER INFORMATION: /note= "Xaa is a basic amino acid."

(ix) FEATURE:
        (A) NAME/KEY: Region
        (B) LOCATION: 13
        (D) OTHER INFORMATION: /note= "Xaa is a basic amino acid."

(xi) SEQUENCE DESCRIPTION: SEQ ID NO:20:

Xaa Xaa Xaa Xaa Xaa Xaa Xaa Xaa Xaa Xaa Xaa Xaa Xaa
1               5                   10

(2) INFORMATION FOR SEQ ID NO:21:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Ala Lys Lys Gln Arg Phe Arg His Arg Asn Arg Lys Gly Tyr Arg Ser
1               5                   10                  15

(2) INFORMATION FOR SEQ ID NO:22:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 2
        (D) OTHER INFORMATION: /note= "Xaa is a basic amino acid."

(ix) FEATURE:
        (A) NAME/KEY: Region
        (B) LOCATION: 3
        (D) OTHER INFORMATION: /note= "Xaa is a basic amino acid."

(ix) FEATURE:
        (A) NAME/KEY: Region
        (B) LOCATION: 5
        (D) OTHER INFORMATION: /note= "Xaa is a basic amino acid."

(ix) FEATURE:
        (A) NAME/KEY: Region
        (B) LOCATION: 7
        (D) OTHER INFORMATION: /note= "Xaa is a basic amino acid."

(ix) FEATURE:
        (A) NAME/KEY: Region
        (B) LOCATION: 9
        (D) OTHER INFORMATION: /note= "Xaa is a basic amino acid."

(ix) FEATURE:
        (A) NAME/KEY: Region
        (B) LOCATION: 11..12
        (D) OTHER INFORMATION: /note= "Xaa is a basic amino acid."

(ix) FEATURE:
        (A) NAME/KEY: Region
        (B) LOCATION: 15
        (D) OTHER INFORMATION: /note= "Xaa is a basic amino acid."

(xi) SEQUENCE DESCRIPTION: SEQ ID NO:22:

Xaa Xaa Xaa Xaa Xaa Xaa Xaa Xaa Xaa Xaa Xaa Xaa Xaa Xaa Xaa Xaa
1               5                   10                  15

(2) INFORMATION FOR SEQ ID NO:23:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Thr Tyr Ile Ser Lys Lys His Ala Glu Lys His Trp Phe
 1               5                  10
```

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 5..7
        (D) OTHER INFORMATION: /note= "Xaa is a basic amino acid."

(ix) FEATURE:
        (A) NAME/KEY: Region
        (B) LOCATION: 10..11
        (D) OTHER INFORMATION: /note= "Xaa is a basic amino acid."

(xi) SEQUENCE DESCRIPTION: SEQ ID NO:24:

```
Xaa Xaa Xaa Xaa Xaa Xaa Xaa Xaa Xaa Xaa Xaa Xaa Xaa
 1               5                  10
```

(2) INFORMATION FOR SEQ ID NO:25:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Ala Thr Pro Ile Arg His Arg Pro Arg Pro Tyr
 1               5                  10
```

(2) INFORMATION FOR SEQ ID NO:26:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 5..7
        (D) OTHER INFORMATION: /note= "Xaa is a basic amino acid."

(ix) FEATURE:
        (A) NAME/KEY: Region
        (B) LOCATION: 9
        (D) OTHER INFORMATION: /note= "Xaa is a basic amino acid."

(xi) SEQUENCE DESCRIPTION: SEQ ID NO:26:

Xaa Xaa Xaa Xaa Xaa Xaa Xaa Xaa Xaa Xaa Xaa
1               5                   10

(2) INFORMATION FOR SEQ ID NO:27:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Lys Thr Lys Arg Ala Arg Lys Lys Gln Arg Val Lys
1               5                   10

(2) INFORMATION FOR SEQ ID NO:28:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: 1
        (D) OTHER INFORMATION: /note= "Xaa is a basic amino acid."

(ix) FEATURE:
        (A) NAME/KEY: Region
        (B) LOCATION: 3..8
        (D) OTHER INFORMATION: /note= "Xaa is a basic amino acid."

(ix) FEATURE:
        (A) NAME/KEY: Region
        (B) LOCATION: 10
        (D) OTHER INFORMATION: /note= "Xaa is a basic amino acid."

(ix) FEATURE:
        (A) NAME/KEY: Region
        (B) LOCATION: 12
        (D) OTHER INFORMATION: /note= "Xaa is a basic amino acid."

(xi) SEQUENCE DESCRIPTION: SEQ ID NO:28:

Xaa Xaa Xaa Xaa Xaa Xaa Xaa Xaa Xaa Xaa Xaa Xaa
1               5                   10

(2) INFORMATION FOR SEQ ID NO:29:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Lys Thr Lys Arg Lys Lys Lys Lys Gln Arg Pro Val
1               5                   10

(2) INFORMATION FOR SEQ ID NO:30:

(i) SEQUENCE CHARACTERISTICS:
        (A) LENGTH: 12 amino acids
        (B) TYPE: amino acid

```
            (C) STRANDEDNESS: single
            (D) TOPOLOGY: linear (ii) MOLECULE TYPE: peptide (ix) FEATURE:
            (A) NAME/KEY: Region
            (B) LOCATION: 1
            (D) OTHER INFORMATION: /note= "Xaa is a basic amino acid."

(ix) FEATURE:
            (A) NAME/KEY: Region
            (B) LOCATION: 3..8
            (D) OTHER INFORMATION: /note= "Xaa is a basic amino acid."

(ix) FEATURE:
            (A) NAME/KEY: Region
            (B) LOCATION: 10
            (D) OTHER INFORMATION: /note= "Xaa is a basic amino acid."

(xi) SEQUENCE DESCRIPTION: SEQ ID NO:30:

Xaa Xaa Xaa Xaa Xaa Xaa Xaa Xaa Xaa Xaa Xaa Xaa
1               5                   10
```